(12) United States Patent
Ding

(10) Patent No.: US 8,952,123 B1
(45) Date of Patent: Feb. 10, 2015

(54) DIOXANONE-BASED COPOLYMERS FOR IMPLANTABLE DEVICES

(75) Inventor: Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1396 days.

(21) Appl. No.: 11/888,808

(22) Filed: Aug. 1, 2007

Related U.S. Application Data

(60) Provisional application No. 60/835,287, filed on Aug. 2, 2006.

(51) Int. Cl.
*C08G 63/66* (2006.01)
*C08G 63/78* (2006.01)

(52) U.S. Cl.
CPC ............... *C08G 63/66* (2013.01); *C08G 63/78* (2013.01)
USPC ............................ 528/361; 528/271; 528/425

(58) Field of Classification Search
None
See application file for complete search history.

(56) References Cited

U.S. PATENT DOCUMENTS

| | | | |
|---|---|---|---|
| 5,076,807 A * | 12/1991 | Bezwada et al. | 606/230 |
| 5,272,012 A | 12/1993 | Opolski | |
| 5,322,925 A * | 6/1994 | Muth et al. | 528/354 |
| 5,403,347 A * | 4/1995 | Roby et al. | 606/230 |
| 5,510,077 A * | 4/1996 | Dinh et al. | 264/485 |
| 5,522,841 A * | 6/1996 | Roby et al. | 606/230 |
| 5,702,754 A | 12/1997 | Zhong | |
| 5,889,075 A * | 3/1999 | Roby et al. | 522/87 |
| 5,997,517 A | 12/1999 | Whitbourne | |
| 6,001,117 A | 12/1999 | Huxel et al. | |
| 6,110,483 A | 8/2000 | Whitbourne et al. | |
| 6,153,252 A * | 11/2000 | Hossainy et al. | 427/2.3 |
| 6,258,382 B1 * | 7/2001 | Takaoka et al. | 424/486 |
| 6,274,164 B1 | 8/2001 | Novich | |
| 6,306,176 B1 | 10/2001 | Whitbourne | |
| 6,494,862 B1 | 12/2002 | Ray et al. | |
| 6,503,538 B1 | 1/2003 | Chu et al. | |
| 6,544,223 B1 | 4/2003 | Kokish | |
| 6,544,543 B1 | 4/2003 | Mandrusov et al. | |
| 6,656,216 B1 | 12/2003 | Hossainy | |
| 6,656,506 B1 | 12/2003 | Wu et al. | |
| 6,663,662 B2 | 12/2003 | Pacetti et al. | |
| 6,663,880 B1 | 12/2003 | Roorda et al. | |
| 6,673,154 B1 | 1/2004 | Pacetti et al. | |
| 6,703,040 B2 | 3/2004 | Katsarava | |
| 6,712,845 B2 | 3/2004 | Hossainy | |
| 6,743,462 B1 | 6/2004 | Pacetti | |
| 6,753,071 B1 | 6/2004 | Pacetti | |
| 6,758,859 B1 | 7/2004 | Dang et al. | |
| 6,790,228 B2 | 9/2004 | Hossainy | |
| 6,818,063 B1 | 11/2004 | Kerrigan | |
| 6,824,559 B2 | 11/2004 | Michal | |
| 6,926,919 B1 | 8/2005 | Hossainy et al. | |
| 6,972,054 B2 | 12/2005 | Kerrigan | |
| 7,005,137 B1 | 2/2006 | Hossainy et al. | |
| 7,022,334 B1 | 4/2006 | Ding | |
| 7,056,591 B1 | 6/2006 | Pacetti et al. | |
| 7,060,093 B2 | 6/2006 | Dang et al. | |
| 7,074,276 B1 | 7/2006 | Van Sciver et al. | |
| 7,115,300 B1 | 10/2006 | Hossainy | |
| 7,135,038 B1 | 11/2006 | Limon | |
| 7,166,680 B2 | 1/2007 | DesNoyer et al. | |
| 7,169,178 B1 | 1/2007 | Santos et al. | |
| 7,175,874 B1 | 2/2007 | Pacetti | |
| 7,201,935 B1 | 4/2007 | Claude et al. | |
| 7,217,426 B1 | 5/2007 | Hossainy | |
| 7,232,490 B1 | 6/2007 | Hossainy | |
| 7,232,573 B1 | 6/2007 | Ding | |
| 2003/0073961 A1 | 4/2003 | Happ | |
| 2003/0082368 A1 | 5/2003 | Reuter et al. | |
| 2003/0104028 A1 | 6/2003 | Hossainy et al. | |
| 2003/0105518 A1 | 6/2003 | Dutta | |
| 2003/0158517 A1 | 8/2003 | Kokish | |
| 2004/0047980 A1 | 3/2004 | Pacetti et al. | |
| 2004/0052858 A1 | 3/2004 | Wu et al. | |
| 2004/0054104 A1 | 3/2004 | Pacetti | |
| 2004/0060508 A1 | 4/2004 | Pacetti et al. | |
| 2004/0062853 A1 | 4/2004 | Pacetti et al. | |
| 2004/0063805 A1 | 4/2004 | Pacetti et al. | |
| 2004/0071861 A1 | 4/2004 | Mandrusov et al. | |
| 2004/0072922 A1 | 4/2004 | Hossainy et al. | |
| 2004/0073298 A1 | 4/2004 | Hossainy | |
| 2004/0086542 A1 | 5/2004 | Hossainy et al. | |
| 2004/0132923 A1 * | 7/2004 | Shalaby | 525/418 |

(Continued)

FOREIGN PATENT DOCUMENTS

WO  WO 03/068289  *  8/2003

OTHER PUBLICATIONS

Han Hyo-Kyung, "Targeted Prodrug Design to Optimize Drug Delivery," AAPS Pharmsci, 2000, 2(1): 1-11.*
Derivative definition from http://cancerweb.ncl.ac.uk/cgi-bin/omd?query=derivative, pp. 1-5. Accessed Jul. 7, 2005.*

(Continued)

*Primary Examiner* — Maury Audet
*Assistant Examiner* — Fred Reynolds
(74) *Attorney, Agent, or Firm* — Squire Patton Boggs (US) LLP

(57) ABSTRACT

The present invention is directed to polymeric materials comprising biodegradable, dioxanone-based copolymers and implantable devices (e.g., drug-delivery stents) formed of such materials. The polymeric materials can also contain at least one additional biocompatible moiety, at least one non-fouling moiety, at least one biobeneficial material, at least one bioactive agent, or a combination thereof. The polymeric materials are designed to improve the mechanical, physical and biological properties of implantable devices formed thereof.

61 Claims, No Drawings

(56) References Cited

U.S. PATENT DOCUMENTS

| | | |
|---|---|---|
| 2004/0180132 A1 | 9/2004 | Pacetti |
| 2004/0191405 A1 | 9/2004 | Kerrigan |
| 2004/0253203 A1 | 12/2004 | Hossainy et al. |
| 2005/0021127 A1 | 1/2005 | Kawula |
| 2005/0025799 A1 | 2/2005 | Hossainy et al. |
| 2005/0036946 A1* | 2/2005 | Pathak et al. .......... 424/9.4 |
| 2005/0048121 A1* | 3/2005 | East et al. .......... 424/486 |
| 2005/0074544 A1 | 4/2005 | Pacetti et al. |
| 2006/0014720 A1* | 1/2006 | Hossainy et al. .......... 514/56 |

OTHER PUBLICATIONS

US pharmacopeia monograph on absorbable surgical sutures, official Jan. 1, 2007.*
Sarasua, J. R. et al; "Crystallinity and mechanical properties of optically pure polylactides and their blends." Polymer Eng. Sci. (2005) 45(5) p. 745-753.*
U.S. Appl. No. 10/104,772, filed Mar. 20, 2002, Dutta.
U.S. Appl. No. 10/718,976, filed Nov. 20, 2003, Hossainy et al.
U.S. Appl. No. 10/812,780, filed Mar. 29, 2004, Tang et al.
U.S. Appl. No. 10/902,982, filed Jul. 30, 2004, Pacetti et al.

* cited by examiner

DIOXANONE-BASED COPOLYMERS FOR IMPLANTABLE DEVICES

CLAIM OF PRIORITY UNDER 35 U.S.C. §119

The present Application for Patent claims priority to Provisional Application Ser. No. 60/835,287, entitled "Polydioxanone-Based Copolymer Stent Coating" and filed on Aug. 2, 2006, which is assigned to the assignee hereof and expressly incorporated by reference in its entirety herein.

BACKGROUND

1. Field of the Invention

The present invention is directed to polymeric materials comprising biodegradable copolymers, implantable devices (e.g., drug-delivery stents) formed of such materials, and therapeutic methods using such devices.

2. Description of the State of the Art

Angioplasty is a well-known procedure for treating heart disease. A problem associated with angioplasty includes formation of intimal flaps or torn arterial linings which can collapse and occlude the conduit after the balloon is deflated. Moreover, thrombosis and restenosis of the artery may develop over several months after angioplasty, which may require another angioplasty procedure or a surgical by-pass operation. "Stenosis" refers to a narrowing or constriction of the diameter of a bodily passage or orifice, and "restenosis" refers to the reoccurrence of stenosis in a blood vessel or heart valve after it has been treated (as by balloon angioplasty, stenting, or valvuloplasty) with apparent success.

Stents are often used in the treatment of atherosclerotic stenoses in blood vessels. To reduce the partial or total occlusion of the artery by the collapse of arterial lining and to reduce the chance of thrombosis and restenosis following angioplasty in the vascular system, a stent can be implanted in the lumen to reinforce body vessels and maintain the vascular patency. A "lumen" refers to a cavity of a tubular organ such as a blood vessel. As a mechanical intervention, stents act as scaffoldings, functioning to physically hold open and, if desired, to expand the wall of a passageway, e.g., a blood vessel, urinary tract or bile duct.

Stents are also used as a vehicle for providing biological therapy. Biological therapy can be achieved by medicating the stents. Medicated stents provide for the local administration of a therapeutic substance at the diseased site, thereby possibly avoiding side effects associated with systemic administration of such medication. One method of medicating stents involves the use of a polymeric carrier coated over the surface of a stent, wherein a therapeutic substance is impregnated in the polymeric carrier.

Late stent thrombosis has emerged as a concern for drug-delivery stents. The incidence of late stent thrombosis appears to be higher with drug-delivery stents than with the corresponding bare metal stents. One potential cause of late thrombosis with drug-delivery stents is a chronic inflammatory or hypersensitivity response to the polymeric coating on the stent.

The present invention addresses late stent thrombosis and offers other advantageous features.

SUMMARY OF THE INVENTION

The present invention is directed to biodegradable polymeric materials used for implantable devices (e.g., stents) that enable the devices to perform their functions more effectively and avoid adverse effects. The polymeric materials are configured to completely or substantially completely erode after the devices accomplish their intended functions (e.g., maintaining vascular patency and locally delivering drugs), thereby avoiding adverse effects such as late stent thrombosis. Other advantages of the biodegradable polymeric materials include, among others, good mechanical properties (e.g., toughness and flexibility), control of drug-release rates, and enhanced adhesion to metal surfaces.

Some embodiments of the invention are directed to a composition comprising a biodegradable copolymer, wherein the copolymer:

is derived from dioxanone and at least one additional ester-, carbonate- or ether-based monomer;
has a crystallinity of about 80% or less;
has a $T_g$ from about $-100°$ C. to about $100°$ C.;
has a polymer number-average molecular weight ($M_n$) from about 10 kDa to about 1,500 kDa; and
completely or substantially completely degrades within about 24 months.

In one embodiment, the at least one additional ester-, carbonate- or ether-based monomer is selected from glycolide (GA), D-lactide (DLA), L-lactide (LLA), D,L-lactide (DLLA), $C_3$-$C_{12}$ β-lactone, $C_4$-$C_{12}$ γ-lactone, α-bromo-γ-butyrolactone, α-bromo-γ-valerolactone, homoserine lactone $C_2$-$C_{14}$ amide, $C_5$-$C_{14}$ δ-lactone, mevalonolactone, $C_6$-$C_{16}$ ε-lactone, 1,3-dioxolan-2-one, 4-methyl-1,3-dioxolan-2-one, 4-methoxymethyl-1,3-dioxolan-2-one, 4-chloro-1,3-dioxolan-2-one, 4-phenyl-1,3-dioxolan-2-one, 4-vinyl-1,3-dioxolan-2-one, trimethylene carbonate (TMC), ethylene oxide (EO), and propylene oxide (PPO). In a particular embodiment, the at least one additional ester-, carbonate- or ether-based monomer is selected from GA, DLA, LLA, DLLA, β-propiolactone (PL), β-butyrolactone (BL), δ-valerolactone (VL), ε-caprolactone (CL), TMC, EO, and PPO.

In an embodiment, the copolymer is derived from dioxanone (DS) and one to three additional ester-based monomers, carbonate-based monomers, ether-based monomers or a combination thereof, and the individual units of each different type of monomer can be arranged in any manner. In a more specific embodiment, the copolymer is selected from P(DS-GA), P(DS-DLA), P(DS-LLA), P(DS-DLLA), P(DS-PL), P(DS-BL), P(DS-VL), P(DS-CL), P(DS-TMC), P(DS-EO), P(DS-PPO), P(DS-GA-DLA), P(DS-GA-LLA), P(DS-GA-DLLA), P(DS-GA-VL), P(DS-GA-CL), P(DS-GA-TMC), P(DS-GA-EO), P(DS-GA-PPO), P(DS-DLA-LLA), P(DS-DLA-DLLA), P(DS-DLA-VL), P(DS-DLA-CL), P(DS-DLA-TMC), P(DS-DLA-EO), P(DS-DLA-PPO), P(DS-LLA-DLLA), P(DS-LLA-VL), P(DS-LLA-CL), P(DS-LLA-TMC), P(DS-LLA-EO), P(DS-LLA-PPO), P(DS-DLLA-VL), P(DS-DLLA-CL), P(DS-DLLA-TMC), P(DS-DLLA-EO), P(DS-DLLA-PPO), P(DS-VL-CL), P(DS-VL-TMC), P(DS-VL-EO), P(DS-VL-PPO), P(DS-CL-TMC), P(DS-CL-EO), P(DS-CL-PPO), P(DS-GA-DLLA-CL), P(DS-GA-DLLA-TMC), P(DS-GA-DLLA-EO), P(DS-GA-CL-TMC), P(DS-GA-CL-EO), P(DS-GA-TMC-EO), P(DS-DLLA-CL-TMC), P(DS-DLLA-CL-EO), P(DS-DLLA-TMC-EO), and P(DS-CL-TMC-EO).

In some embodiments, the composition further comprises at least one additional biocompatible moiety, at least one non-fouling moiety, at least one biobeneficial material, at least one biologically active agent, or a combination thereof.

Other embodiments are drawn to coatings comprising the inventive composition and implantable devices formed of a material comprising the inventive composition. In an embodiment, the material is a coating disposed over at least a portion of the implantable device.

In certain embodiments, the implantable device is selected from stents, grafts, stent-grafts, catheters, leads and electrodes, clips, shunts, closure devices, valves, and particles. In a particular embodiment, the implantable device is a stent.

Further embodiments of the invention are directed to a method of treating or preventing a condition or disorder in a patient, comprising implanting in the patient an implantable device formed of a material comprising the inventive composition, wherein the condition or disorder is selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In one embodiment, the material is a coating disposed over at least a portion of the implantable device.

Various embodiments of the invention are described in further detail below.

DETAILED DESCRIPTION OF THE INVENTION

Terms and Definitions

The following definitions apply:

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Complete degradation" of a polymer or a polymeric material (e.g., a polymeric coating) means that the polymer or the polymeric material loses at least about 95% of its mass over a period of time.

"Substantially complete degradation" of a polymer or a polymeric material (e.g., a polymeric coating) means that the polymer or the polymeric material loses at least about 75% of its mass over a period of time. In certain embodiments, "substantially complete degradation" of a polymer or a polymeric material can mean that the polymer or the polymeric material loses at least about 80% of its mass, or at least about 85% of its mass, or at least about 90% of its mass, or at least about 95% of its mass over a period of time.

As used herein, a "biocompatible moiety" refers to a moiety that is capable of enhancing the biological compatibility of the composition, material (e.g., coating) or structure (e.g., implantable device) containing it by not causing injury or toxicity to, or an immunological reaction in, living tissue.

A "biobeneficial material" refers to a material that benefits a treatment site (e.g., by enhancing the biocompatibility of the medical device containing such material) by being non-fouling, hemocompatible, non-thrombogenic, and/or anti-inflammatory, etc., without depending on the release of a pharmaceutically or therapeutically active agent.

A "non-fouling moiety" refers to a moiety that provides an implantable device fabricated from or coated with a material comprising the moiety with the ability to resist (i.e., to prevent, delay, or reduce the amount of) build-up of a denatured layer of protein on its surface, which is caused by the body's reaction to foreign material and could lead to protein fouling. The adsorption of proteins on the surface of an implanted device constitutes the first step of several biological responses, including the activation of the coagulation cascade. Following protein adsorption, cell adhesion occurs, which could lead to impairment of the device's functioning as well as adverse side effects on the patient. For example, thrombi formation could occur after adsorption and activation of platelets.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal".

In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N.J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs*, 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

The terms "block copolymer" and "graft copolymer" are defined in accordance with the terminology used by the International Union of Pure and Applied Chemistry (IUPAC). "Block copolymer" refers to a copolymer containing a linear arrangement of blocks. The block is defined as a portion of a polymer molecule in which the monomer units have at least one constitutional or configurational feature absent from the adjacent portions. "Graft copolymer" refers to a polymer composed of macromolecules with one or more species of block connected to the main chain as side chains, these side chains having constitutional or configurational features that differ from those in the main chain.

As used herein, an "implantable device" can be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-delivery particles, microparticles and nanoparticles). The stents can be intended for any vessel in the body, including neurological, carotid, vein graft, coronary, aortic, renal, iliac, femoral, popliteal vasculature, and urethral passages.

An implantable device can be designed for the localized delivery of a therapeutic agent. A medicated implantable device can be constructed in part, e.g., by coating the device with a coating material containing a therapeutic agent. The body of the device can also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a "portion" of an implantable device can be any portion of the device. For example, a portion can be a portion of the body of the device. As another example, a portion can be a portion of the surface of the device, or the whole surface of the device. As a further example, a portion can refer to an area of material in the body or over the surface of the device, e.g., a layer, film or coating disposed over the device.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon-expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn, which allows the stent to self-expand.

The "glass transition temperature", $T_g$, is the temperature at which the amorphous domains of a polymer change from a brittle, glassy, vitreous state to a solid deformable, ductile or rubbery state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. The $T_g$ of a given polymer can be dependent on the heating rate and can be influenced by the thermal history of the polymer. Furthermore, the chemical structure of the polymer heavily influences the glass transition by affecting chain mobility.

The "melting temperature", $T_m$, is the temperature at which the crystalline domains of a polymer lose their short- and long-term order, changing from a regular, ordered structure of chain packing to that of a disordered structure, resembling an amorphous polymer. The disappearance of the polymer crystalline phase is accompanied by changes in physical properties of the polymer. The material becomes a viscous solid, with discontinuous changes in the density, refractive index, heat capacity, transparency, and other properties. The $T_m$ of a given polymer occurs over a finite temperature range. The breadth of the transition is dependent on the size and perfection of the polymer crystallites, as well as their homogeneity and purity. By thermal analytical techniques, the $T_m$ of a semi-crystalline polymer is an endothermic transition when the heating rate is positive. The ability of the polymer chains to pack into an ordered, repeating structure is heavily influenced by the chemical structure of the polymer.

"Strength" refers to the maximum stress along an axis which a material will withstand prior to fracture. The ultimate strength is calculated from the maximum load applied during the test divided by the original cross-sectional area.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

The terms "alkyl" and "aliphatic group" refer to an optionally substituted, straight-chain or branched, saturated or unsaturated hydrocarbon moiety that may contain one or more heteroatoms selected from O, S, and N. If unsaturated, the alkyl or aliphatic group may contain one or more double bonds and/or one or more triple bonds. The alkyl or aliphatic group may be monovalent (i.e., —R) or divalent (i.e., —R—) in terms of its attachment to the rest of the compound. Examples of alkyl and aliphatic groups include, but are not limited to, methyl, ethyl, ethylenyl, ethynyl, n-propyl, isopropyl, propenyl, propynyl, n-butyl, isobutyl, sec-butyl, tertiary-butyl, butenyl, butynyl, n-pentyl, isopentyl, pentenyl, and pentynyl.

The terms "heteroalkyl" and "heteroaliphatic group" refer to an alkyl or aliphatic group that contains at least one heteroatom selected from O, S and N, in the main portion and/or the branch(es) of the hydrocarbon moiety. Examples of heteroalkyl and heteroaliphatic groups include, but are not limited to, alcohols, ethers, oxo compounds, ketones, aldehydes, esters, carbonates, thioesters, thiols, sulfides, sulfoxides, sulfones, sulfonamides, amino compounds, amines, nitriles, N-oxides, imines, oximes, amides, carbamates, ureas, and thioureas.

The terms "cycloalkyl" and "cycloaliphatic group" refer to an optionally substituted, saturated or unsaturated, mono- or polycyclic hydrocarbon moiety that may contain one or more heteroatoms selected from O, S, and N. If unsaturated, the cycloalkyl or cycloaliphatic group may contain one or more double bonds and/or one or more triple bonds in and/or off of one or more rings of the cyclic moiety. The cycloalkyl or cycloaliphatic group may be monovalent (i.e., -Cyc) or divalent (i.e., -Cyc-) in terms of its attachment to the rest of the compound. Examples of cycloalkyl and cycloaliphatic groups include, but are not limited to, cyclopropyl, cyclobutyl, cyclopentyl, cyclopentenyl, cyclohexyl, cyclohexenyl, decahydronaphthyl, and octahydroindyl.

The terms "heterocycloalkyl" and "heterocycloaliphatic group" refer to a cycloalkyl or cycloaliphatic group in which at least one ring in the cyclic moiety contains one or more heteroatoms selected from O, S, and N. Examples of heterocycloalkyl and heterocycloaliphatic groups include, but are not limited to, aziridinyl, oxiranyl, oxolanyl, thiolanyl, pyrrolidinyl, 3-pyrrolinyl, dioxalanyl, 1,3-dithiolanyl, oxazolidinyl, imidazolidinyl, oxanyl, piperidinyl, piperazinyl, 1,3-dioxanyl, 1,4-dioxanyl, morpholinyl, octahydroindolyl, octahydroisoindolyl, octahydrobenzofuryl, octahydrobenzothiophene, octahydrochromenyl, and decahydroquinolinyl.

The terms "aryl" and "aromatic group" refer to an optionally substituted mono- or polycyclic aromatic moiety in which at least one ring in the moiety is aromatic. The ring(s) in the moiety may be carbocyclic or may contain one or more heteroatoms selected from O, S, and N. The ring(s) in the moiety may be aromatic or non-aromatic (saturated or unsaturated), but at least one ring in the moiety is aromatic. An aryl or aromatic group may be monovalent (i.e., -Ar) or divalent (i.e., -Ar-) in terms of its attachment to the rest of the compound. Examples of aryl and aromatic groups include, but are not limited to, phenyl, indolinyl, isoindolinyl, 2,3-dihydrobenzofuryl, 2,3-dihydrobenzothiophene, chromanyl, 1,2,3,4-tetrahydroquinolinyl, 1,2,3,4-tetrahydroisoquinolinyl, naphthyl, indenyl, and indanyl.

The terms "heteroaryl" and "heteroaromatic group" refer to an aryl or aromatic group in which at least one ring (aromatic or non-aromatic) in the aromatic moiety contains one or more heteroatoms selected from O, S, and N. Examples of heteroaryl and heteroaromatic groups include, but are not limited to, pyrrolyl, pyrazolyl, imidazolyl, furyl, isoxazolyl, oxazolyl, thiophenyl, thiazolyl, isothiazolyl, triazolyl, oxadiazolyl, thiadiazolyl, tetrazolyl, pyridyl, pyridazinyl, pyrimidinyl, pyrazinyl, 1,3,5-triazinyl, indolyl, isoindolyl, benzofuranyl, benzothiophenyl, indazolyl, benzimidazolyl, benzothiazolyl, [1,7]naphthyridinyl, chromenyl, quinolinyl, isoquinolinyl, cinnolinyl, quinazolinyl, quinoxalinyl, phthalazinyl, purinyl, pyridazinyl, quinolinyl, imidazo[4,5-c]pyridinyl, pyrido[2,3-d]pyrimidinyl, pyrimido[3,2-c]pyrimidinyl, and pyrrolo[2,3-d]pyrimidinyl.

The alkyl, aliphatic, heteroalkyl, heteroaliphatic, cycloalkyl, cycloaliphatic, heterocycloalkyl, heterocycloaliphatic, aryl, aromatic, heteroaryl and heteroaromatic groups may be substituted or unsubstituted. If substituted, they may contain from 1 to 5 substituents. The substituents include, but are not limited to: optionally substituted carbon-containing groups, e.g., alkyl, cycloalkyl and aryl (e.g., benzyl); halogen atoms (i.e., F, Cl, Br and I) and optionally substituted halogen-containing groups, e.g., haloalkyl (e.g., trifluoromethyl); optionally substituted oxygen-containing groups, e.g., oxo, alcohols (e.g., hydroxyl, hydroxyalkyl, aryl (hydroxyl)alkyl), and ethers (e.g., alkoxy, aryloxy, alkoxyalkyl, aryloxyalkyl); optionally substituted carbonyl-containing groups, e.g., aldehydes (e.g., carboxaldehyde), ketones (e.g., alkylcarbonyl, alkylcarbonylalkyl, arylcarbonyl, arylalkylcarbonyl, arycarbonylalkyl), carboxy acids (e.g., carboxy, carboxyalkyl), esters (e.g., alkoxycarbonyl, alkoxycarbonylalkyl, alkylcarbonyloxy, alkylcarbonyloxyalkyl), carbonates, thioesters, amides (e.g., aminocarbonyl, mono- or dialkylaminocarbonyl, aminocarbonylalkyl, mono- or dialkylaminocarbonylalkyl, arylaminocarbonyl, alkylarylaminocarbonyl), carbamates (e.g., alkoxycarbonylamino, arloxycarbonylamino, aminocarbonyloxy, mono- or dialkylaminocarbonyloxy, arylaminocarbonyloxy, alkylarylaminocarbonyloxy), and ureas (e.g., mono- or dialkylaminocarbonylamino, arylaminocarbonylamino, alkylarylaminocarbonylamino); optionally substituted groups containing carbonyl derivatives, e.g., imines, oximes, and thioureas; optionally substituted nitrogen-containing groups, e.g., amines (e.g., amino, mono- or dialkylamino, mono- or diarylamino, alkylarylamino, aminoalkyl, mono- or dialkylaminoalkyl), azides, nitriles (e.g., cyano, cyanoalkyl) and nitro; optionally substituted sulfur-containing groups, e.g., thiols, sulfides, thioethers, sulfoxides, sulfones and sulfonamides (e.g. sulfhydryl, alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and optionally substituted aromatic or non-aromatic heterocyclic groups containing one or more heteroatoms selected from O, S and N (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthyridinyl, cinnolinyl, quinazolinyl, pyridopyridyl, benzoxazinyl, quinoxalinyl, chromenyl, chromanyl, isochromanyl, phthalazinyl, carbolinyl).

EMBODIMENTS OF THE INVENTION

Composition and Polymer

The polymeric materials of the present invention are designed to possess certain advantages over conventional biodegradable polymers used to make implantable devices. The mechanical properties (e.g., strength, rigidity, fracture toughness and flexibility) and physical properties (e.g., $T_g$, degradation rate and drug permeability) of a polymer can be tuned by the appropriate selection of monomers and ratio and arrangement thereof. To improve the biological properties of an implantable device formed of a material comprising the polymer, at least one additional biocompatible moiety, at least one non-fouling moiety, at least one biobeneficial material and/or at least one bioactive agent can be physically or chemically attached to, blended with, or incorporated with the polymer. Finally, adhesion of a polymeric coating to a metal surface can be promoted by appropriate (e.g., chemical) modification of the polymer. Such modification could lead to a single polymer, which could be used as a drug reservoir, with no primer.

Dioxanone would make a suitable monomer component for a polymer that needs to be biodegradable and flexible, e.g., a polymer used to make a coating disposed over an implantable device. Polydioxanone (PDS®), which is synthesized via ring opening polymerization of dioxanone (DS), is completely or substantially completely absorbed in vivo within about 6 months. It has from about 30% to about 50% crystallinity and a $T_g$ from about −16° C. to about 0° C. These physical properties make PDS relatively elastic compared to, e.g., polyglycolide (PGA) and poly(D-lactide) (PDLA). Depending on various other factors (e.g., the identity and ratio of other monomer components), a DS-based copolymer can exhibit suitable elasticity to be used in forming an implantable device that changes its shape (e.g., a stent that is crimped during delivery but expands during deployment).

Accordingly, some embodiments of the present invention, optionally in combination with one or more other embodiments described herein, are directed to a composition comprising a biodegradable copolymer, wherein the copolymer:
  is derived from dioxanone and at least one additional ester-, carbonate- or ether-based monomer;
  has a crystallinity of about 80% or less;
  has a $T_g$ from about −100° C. to about 100° C.;
  has a polymer number-average molecular weight ($M_n$) from about 10 kDa to about 1,500 kDa; and
  completely or substantially completely degrades within about 24 months.

In a narrower embodiment, optionally in combination with one or more other embodiments described herein, the copolymer:
  has a crystallinity from about 5% to about 70%;
  has a $T_g$ from about −60° C. to about 60° C.;
  has an $M_n$ from about 20 kDa to about 1,000 kDa; and
  completely or substantially completely degrades within about 12 months.

In an even narrower embodiment, optionally in combination with one or more other embodiments described herein, the copolymer:
  has a crystallinity from about 10% to about 60%;
  has a $T_g$ from about −30° C. to about 30° C.;
  has an $M_n$ from about 30 kDa to about 700 kDa; and
  completely or substantially completely degrades within about 6 months.

In an embodiment, optionally in combination with one or more other embodiments described herein, the copolymer is derived from dioxanone (DS) and one to five additional ester-based monomers, carbonate-based monomers, ether-based monomers or a combination thereof, and the individual units of each different type of monomer can be arranged in any manner. In other embodiments, the copolymer is derived from DS and one to four, or one to three, or one to two, additional ester-based monomers, carbonate-based monomers, ether-based monomers, or a combination thereof. Dioxanone can be 1,4-dioxanone or 1,3-dioxanone, and thus the scope of the present invention encompasses copolymers derived from 1,4-dioxanone and/or 1,3-dioxanone.

In one embodiment, the copolymer is derived from DS and at least one additional ester-based monomer. In another embodiment, the copolymer is derived from DS and at least one carbonate-based monomer. In yet another embodiment, the copolymer is derived from DS and at least one ether-based monomer. In a further embodiment, the copolymer is derived from DS and any combination of ester-based monomers, carbonate-based monomers, and ether-based monomers.

The dioxanone monomer, ester-based monomers, carbonate-based monomers, and ether-based monomers described herein can optionally be substituted with one to five substituents. The optional substituents can be straight-chain or branched, saturated or unsaturated, cyclic or acyclic, aromatic or nonaromatic, and can contain one or more of the heteroatoms O, N and/or S. The optional substituents can also contain one or more groups that may be straight-chain or branched, saturated or unsaturated, cyclic or acyclic, aromatic or nonaromatic, and that may contain one or more of the heteroatoms O, N and/or S. Non-limiting examples of the optional substituents include: halogens; nitrile; $C_1$-$C_{12}$ alkyl; $C_2$-$C_{12}$ alkenyl; $C_2$-$C_{12}$ alkynyl; $C_1$-$C_{12}$ haloalkyl; $C_1$-$C_{12}$ heteroalkyl; $C_1$-$C_{12}$ alkoxy; $C_1$-$C_{12}$ ethers; $C_1$-$C_{12}$ sulfides; $C_1$-$C_{12}$ thioethers; $C_1$-$C_{12}$ sulfones; $C_1$-$C_{12}$ secondary amines; $C_2$-$C_{24}$ tertiary amines; $C_1$-$C_{12}$ ketones; $C_1$-$C_{12}$ C- and O-linked esters; $C_1$-$C_{12}$ S- and N-linked secondary sulfonamides; $C_2$-$C_{24}$ S- and N-linked tertiary sulfonamides; $C_1$-$C_{12}$ C- and N-linked secondary amides; $C_2$-$C_{24}$ C- and N-linked tertiary amides; $C_1$-$C_{12}$ O- or N-linked secondary carbamates; $C_2$-$C_{24}$ O- or N-linked tertiary carbamates; $C_3$-$C_6$ cycloalkyl; $C_3$-$C_6$ heterocycloalkyl; $C_5$-$C_{14}$ aryl; and $C_5$-$C_{14}$ heteroaryl.

In one embodiment, the copolymer has the specified $T_g$ ranges when it is hydrated. In another embodiment, the copolymer has the specified $T_g$ ranges when it is not hydrated. It should be understood that in some cases, the copolymer may have a $T_m$ rather than a $T_g$, and the scope of the present invention encompasses those cases where the copolymer has a $T_m$ rather than a $T_g$.

The $T_g$ of the copolymer can be tuned to a desired value by appropriate selection of component monomers and adjustment of their number, ratio and arrangement. A higher $T_g$ can increase strength and rigidity. Strength and rigidity may be important for an implantable device formed of a polymeric material in certain applications, e.g., for a stent so that the stent can support the walls of a vessel.

On the other hand, a lower $T_g$ can enhance the fracture toughness and flexibility of the copolymer and improve drug-release control. Toughness and flexibility may be important for a range of aggressive applications of an implantable device, e.g., for a coated stent, such as overlapped stents, stent through stent delivery, and bifurcations. Polymers (e.g., certain glassy, semicrystalline polymers) with too high a $T_g$ may be brittle under physiological conditions and fracture during the application of the device, exhibiting little or no plastic deformation prior to failure.

For a polymer with low permeability of a drug, a high drug/polymer ratio must be employed to get the drug to release. However, a high drug/polymer ratio can lead to a drug-release profile in which most of the drug is released as a burst, and the remaining portion of the drug is released very slowly. On the other hand, a low drug/polymer ratio may result in no drug release at all. A higher drug permeability can allow better control of drug-release rates at reasonable drug-to-polymer ratios, e.g., where the amount of polymer is greater than 50% by weight.

The copolymer of the invention can have any $T_g$ value within the range from about −100° C. to about 100° C. The $T_g$ of the copolymer can be tuned to a desired value depending on the particular applications of the copolymer. In narrower embodiments, the copolymer can have a $T_g$ from about −80° C. to about 80° C., or from about −60° C. to about 60° C., or from about −40° C. to about 40° C., or from about −20° C. to about 20° C., or from about −10° C. to about 10° C. The copolymer can also have a $T_g$ in the lower or higher end of the range. For example, in some embodiments, the copolymer can have a $T_g$ from about −100° C. to about 0° C., or from about −80° C. to about −20° C., or from about −60° C. to about −40° C., or from about −60° C. to about 0° C., or from about −40° C. to about 0° C., or from about −20° C. to about 0° C. In other embodiments, the copolymer can have a $T_g$ from about 0° C. to about 100° C., or from about 20° C. to about 80° C., or from about 40° C. to about 60° C., or from about 0° C. to about 60° C., or from about 0° C. to about 40° C., or from about 0° C. to about 20° C.

The mechanical properties of a polymer can also be influenced by the identity of its monomer components. For example, poly(glycolide) (PGA), poly(D-lactide) (PDLA), poly(L-lactide) (PLLA), and poly(D,L-lactide) (PDLLA) tend to be stronger and more rigid. Thus, in one embodiment, monomer units of glycolide (GA), D-lactide (DLA), L-lactide (LLA), D,L-lactide (DLLA), or a combination thereof are used to increase the strength and rigidity of the inventive copolymer.

On the other hand, non-limiting examples of biodegradable polymers having a relatively high fracture toughness and flexibility at body temperature include polycaprolactone (PCL), poly(trimethylene carbonate) (PTMC), polydioxanone (PDS), poly(propiolactone), poly(valerolactone) and polyacetal. Therefore, to enhance the toughness and flexibility of the copolymer, some embodiments of the copolymer can include caprolactone (CL), trimethylene carbonate (TMC), propiolactone, valerolactone or acetal monomer units, or a combination thereof, in addition to dioxanone (DS) units.

The identity of the monomer components of a polymer can also influence its degradation rate. For example, the copolymer of the invention can include monomer units that are hydrophilic and/or hydrolytically active. These two characteristics increase the moisture content of the copolymer, which increases its degradation rate. The copolymer can also contain monomer units that have acidic or hydrophilic degradation products. Since the rate of the hydrolysis reaction tends to increase as the pH decreases, acidic degradation products can increase the degradation rate of the copolymer.

Non-limiting examples of polymers that degrade rapidly include PDS, PGA, PDLA, PLLA and PDLLA. PDS generates about $0.98 \times 10^{-2}$ moles of acid per gram when it fully degrades, comparable to PGA (about $1.7 \times 10^{-2}$ moles of acid per gram) and PDLA and PLLA (about $1.4 \times 10^{-2}$ moles of acid per gram). The monofilaments of PDS lose about 50% of their initial strength after about 3 weeks as a consequence of degradation, and PDS is completely or substantially completely absorbed in vivo within about 6 months. Accordingly, for faster degradation, some embodiments of the copolymer can include monomer units of GA, DLA, LLA, DLLA, or a combination thereof in addition to DS units.

As a particular example, for faster degradation the copolymer of the invention can contain GA units. When incorporated into a polymer, glycolic acid hydrolyzes faster than L-lactic acid or D-lactic acid, for the ester bond formed from glycolic acid is less sterically hindered than that formed from lactic acid. Further, glycolide units have acidic degradation products that can increase the degradation rate of a GA-containing polymer. Moreover, glycolic acid is a low molecular weight monomer, so that an appreciable level of glycolic acid means that there is a substantial number of ester bonds formed from glycolic acid in a GA-containing polymer, any or all of which can hydrolyze. For example, a fast degrading polymer is poly(glycolide-co-trimethylene carbonate) (P(GA-co-TMC)).

Incorporation of a hydrophilic component or polymer in the inventive copolymer can also enhance its drug permeability as well as its degradation rate and improve control of drug-release rates. Increased water penetration and content in the copolymer owing to the hydrophilic component or polymer increases the permeability of the copolymer to a drug. Non-limiting examples of hydrophilic components or polymers include carboxylic acid-bearing monomers (e.g., methacrylic acid (MA) and acrylic acid (AA)), hydroxyl-bearing monomers (e.g., hydroxyethyl methacrylate (HEMA), hydroxypropyl methacrylate (HPMA), hydroxypropyl methacrylamide, and 3-trimethylsilylpropyl methacrylate (TM-SPMA)), polyalkylene oxide, poly(ethylene glycol) (PEG), poly(propylene glycol), PEG acrylate (PEGA), PEG methacrylate, copolymers of 2-methacryloyloxyethylphosphorylcholine (MPC) and n-vinyl pyrrolidone (VP), hydroxy functional poly(vinyl pyrrolidone) (PVP), SIS-PEG (SIS is polystyrene-polyisobutylene-polystyrene block copolymer), polystyrene-PEG, polyisobutylene-PEG, PCL-PEG, PLA-PEG (PLA is polylactic acid), PMMA-PEG (PMMA is poly(methyl methacrylate)), PDMS-PEG (PDMS is polydimethyloxanone), PVDF-PEG (PVDF is polyvinylidene fluoride), PLURONIC™ surfactants (polypropylene oxide-co-polyethylene glycol), poly(tetramethylene glycol), poly(L-lysine-g-ethylene glycol) (PLL-g-PEG), poly(L-lysine-g-hyaluronic acid) (PLL-g-HA), poly(L-lysine-g-phosphoryl choline) (PLL-g-PC), poly(L-lysine-g-vinyl pyrrolidone) (PLL-g-PVP), poly(ethylimine-g-ethylene glycol) (PEI-g-PEG), poly(ethylimine-g-hyaluronic acid) (PEI-g-HA), poly(ethylimine-g-phosphoryl choline) (PEI-g-PC), poly(ethylimine-g-vinyl pyrrolidone) (PEI-g-PVP), PLL-co-HA, PLL-co-PC, PLL-co-PVP, PEI-co-PEG, PEI-co-HA, PEI-co-PC, PEI-co-PVP, dextran, dextrin, sodium hyaluronate, hyaluronic acid, elastin, chitosan, acrylic sulfate, acrylic sulfonate, acrylic sulfamate, methacrylic sulfate, methacrylic sulfonate, methacrylic sulfamate, polymers and copolymers thereof, and polymers and copolymers of combinations thereof.

In some embodiments, the copolymer of the invention can include toughness-enhancing units and fast degrading units. In more specific embodiments, the copolymer can include GA, CL, TMC, valerolactone, propiolactone or acetal units, or a combination thereof, in addition to DS units. The copolymer can have block, alternating or random GA, CL, TMC, valerolactone, propiolactone and/or acetal units, or any other variations in their arrangement. For example, the copolymer can be poly(DS-co-GA-co-CL), poly(DS-co-GA-co-TMC), or poly(DS-co-GA-co-TMC-co-CL).

The flexibility, toughness and degradation rate of the copolymer can also be tuned by adjusting the ratio of fast degrading and toughness-enhancing units. For example, as the ratio of CL increases and that of GA decreases in poly (DS-co-GA-co-CL), the copolymer becomes more flexible and tougher and less rigid. As another example, the degradation rate of the copolymer can be enhanced by increasing the fraction of GA in poly(DS-co-GA-co-CL) relative to CL. In exemplary embodiments, a DS-based copolymer containing glycolide units can have greater than 1 wt %, 5 wt %, 10 wt %, 20 wt %, 30 wt %, 40 wt %, 50 wt %, 60 wt %, 70 wt % or 80 wt %. GA units.

The degradation rate of the inventive copolymer can also be influenced by its physical state. Since the diffusion rate of fluids through an amorphous structure is generally faster than through a crystalline structure, the copolymer can be configured to have a higher degree of amorphousness to increase its degradation rate. The faster degrading units or sections of the copolymer increase water penetration and content in those units or sections. The increased water penetration and content causes an increase in the degradation rate of the copolymer.

The physical state of the copolymer can also influence its mechanical properties. A more crystalline copolymer can be stronger and more rigid. On the other hand, a more amorphous copolymer can be tougher and more flexible. A more amorphous copolymer can be more "elastomeric" or "rubbery" in that it can exhibit elastic deformation through a greater range of deformation. This characteristic may be desirable when the structure of an implantable device is anticipated to deform during the device's applications, e.g., when a stent that is crimped during delivery expands upon deployment.

In an embodiment, optionally in combination with one or more other embodiments described herein, the copolymer of the invention can have any degree of crystallinity from about 0% to about 80%. In narrower embodiments, the copolymer can have a crystallinity from about 2% to about 75%, or from about 5% to about 70%, or from about 10% to about 65%, or from about 15% to about 60%, or from about 20% to about 55%, or from about 25% to about 50%.

For greater strength and rigidity, the copolymer can have a degree of crystallinity at the higher end of the range. In certain embodiments, optionally in combination with one or more other embodiments described herein, the copolymer can have a crystallinity from about 30% to about 80%, or from about 35% to about 75%, or from about 40% to about 70%, or from about 45% to about 65%.

To increase its toughness, flexibility, degradation rate and drug permeability, the copolymer can be configured to be more amorphous, i.e., be less crystalline. In some embodiments, optionally in combination with one or more other embodiments described herein, the copolymer can have a crystallinity from about 0% to about 60%, or from about 5% to about 55%, or from about 10% to about 50%, or from about 15% to about 45%, or from about 20% to about 40%. In other embodiments, the copolymer can be substantially or completely amorphous. For example, the copolymer can have a degree of crystallinity of about 10% or less, or about 7.5% or less, or about 5% or less.

Depending on the intended applications of an implantable device formed of a polymeric material, the copolymer of the invention can have a wide range of degradation rates. For example, it may be desirable for the copolymer to have a slow degradation rate (e.g., substantially complete degradation over a period of about 2 years) if the device is intended to act as a structural scaffold for an extended period of time. Conversely, faster degradation of the copolymer (e.g., substantially complete degradation over a period of about 6 months or less) may be desired in cases where the device is intended to accomplish its functions within a shorter period of time, e.g., locally delivering a drug up to about 6 months or less. Faster degradation of the copolymer may be advantageous in, e.g., avoiding or minimizing the body's immune response to the polymeric material forming the device, which may be a cause of adverse side effects such as late stent thrombosis.

In an embodiment, optionally in combination with one or more other embodiments described herein, the copolymer of the invention completely or substantially completely degrades within about 24 months. In narrower embodiments, the copolymer completely or substantially completely degrades within about 18 months, or within about 12 months, or within about 6 months, or within about 3 months, or within about 2 months, or within about 1 month (i.e., 30 days).

The mechanical properties (e.g., strength, rigidity, toughness and flexibility) and physical properties (e.g., $T_g$, crystallinity, degradation rate and drug permeability) of the inventive copolymer can be tuned by appropriate selection of monomer components; the number, ratio, and arrangement of the monomer components; the length or molecular weight, weight ratio, and arrangement of any sections of particular monomer component(s) within the copolymer; and any other substances physically or chemically attached to, blended with, or incorporated with the copolymer.

In some embodiments, optionally in combination with one or more other embodiments described herein, the biodegradable copolymer of the invention is derived from dioxanone (DS) and at least one additional ester-, carbonate- or ether-based monomer selected from glycolide (GA), D-lactide (DLA), L-lactide (LLA), D,L-lactide (DLLA), $C_3$-$C_{12}$ β-lactone, $C_4$-$C_{12}$ γ-lactone, α-bromo-γ-butyrolactone, α-bromo-γ-valerolactone, homoserine lactone $C_2$-$C_{14}$ amide, $C_5$-$C_{14}$ δ-lactone, mevalonolactone, $C_6$-$C_{16}$ ε-lactone, 1,3-dioxolan-2-one, 4-methyl-1,3-dioxolan-2-one, 4-methoxymethyl-1,3-dioxolan-2-one, 4-chloro-1,3-dioxolan-2-one, 4-phenyl-1,3-dioxolan-2-one, 4-vinyl-1,3-dioxolan-2-one, trimethylene carbonate (TMC), ethylene oxide (EO), and propylene oxide (PPO). In a particular embodiment, the at least one additional ester-, carbonate- or ether-based monomer is selected from GA, DLA, LLA, DLLA, β-propiolactone (PL), β-butyrolactone (BL), δ-valerolactone (VL), ε-caprolactone (CL), TMC, EO, and PPO.

In certain embodiments, optionally in combination with one or more other embodiments described herein, the copolymer is derived from DS and one to three additional ester-based monomers, carbonate-based monomers and/or ether-based monomers selected from GA, DLA, LLA, DLLA, PL, BL, VL, CL, TMC, EO and PPO, wherein the individual units of each different type of monomer can be arranged in any manner (e.g., block, graft, random, alternating, etc.). In a more specific embodiment, the copolymer is selected from P(DS-GA), P(DS-DLA), P(DS-LLA), P(DS-DLLA), P(DS-PL), P(DS-BL), P(DS-VL), P(DS-CL), P(DS-TMC), P(DS-EO), P(DS-PPO), P(DS-GA-DLA), P(DS-GA-LLA), P(DS-GA-DLLA), P(DS-GA-VL), P(DS-GA-CL), P(DS-GA-TMC), P(DS-GA-EO), P(DS-GA-PPO), P(DS-DLA-LLA), P(DS-DLA-DLLA), P(DS-DLA-VL), P(DS-DLA-CL), P(DS-DLA-TMC), P(DS-DLA-EO), P(DS-DLA-PPO), P(DS-LLA-DLLA), P(DS-LLA-VL), P(DS-LLA-CL), P(DS-LLA-TMC), P(DS-LLA-EO), P(DS-LLA-PPO), P(DS-DLLA-VL), P(DS-DLLA-CL), P(DS-DLLA-TMC), P(DS-DLLA-EO), P(DS-DLLA-PPO), P(DS-VL-CL), P(DS-VL-TMC), P(DS-VL-EO), P(DS-VL-PPO), P(DS- CL-TMC), P(DS-CL-EO), P(DS-CL-PPO), P(DS-GA-DLLA-CL), P(DS-GA-DLLA-TMC), P(DS-GA-DLLA-EO), P(DS-GA-CL-TMC), P(DS-GA-CL-EO), P(DS-GA-TMC-EO), P(DS-DLLA-CL-TMC), P(DS-DLLA-CL-EO), P(DS-DLLA-TMC-EO), and P(DS-CL-TMC-EO).

In some embodiments, optionally in combination with one or more other embodiments described herein, the copolymer of the invention specifically cannot be derived from one or more of any of the monomers described herein. In certain embodiments, the copolymer specifically cannot be any particular one of the polymers or copolymers described herein.

For forming certain types of material (e.g., films, coatings, etc.), the entire polymer may need to have sufficient molecular weight. Accordingly, in one embodiment, optionally in combination with one or more other embodiments described herein, the copolymer of the invention has a polymer number-average molecular weight ($M_n$) of at least about 5 kDa. In other embodiments, the copolymer has an $M_n$ of at least about 10 kDa, or at least about 20 kDa, or at least about 30 kDa, or at least about 40 kDa.

The copolymer of the invention can have a wide range of $M_n$ depending on its intended applications. In an embodiment, optionally in combination with one or more other embodiments described herein, the copolymer has an $M_n$ from about 10 kDa to about 1,5000 kDa. In other embodiments, the copolymer has an $M_n$ from about 15 kDa to about 1,250 kDa, or from about 20 kDa to about 1,000 kDa, or from about 25 kDa to about 750 kDa, or from about 30 kDa to about 500 kDa. A polymer with an $M_n$ from about 20 kDa to about 500 kDa may be more amenable to being processed into a coating. Thus, in one embodiment, the inventive copolymer has an $M_n$ from about 20 kDa to about 500 kDa. In another embodiment, the polymer has an $M_n$ from about 40 kDa to about 500 kDa.

As stated previously, the mechanical and physical properties of the inventive copolymer can be influenced by the number of units of the monomer components and the ratio thereof. In some embodiments of the copolymer, optionally in combination with one or more other embodiments described herein, dioxanone and the at least one additional ester-, carbonate- or ether-based monomer each independently have from about 5 to about 5,000 monomer units. In narrower embodiments, each type of monomer of the copolymer has from about 10 to about 4,500 monomer units, or from about 20 to about 4,000 monomer units, or from about 30 to about 3,500 monomer units, or from about 40 to about 3,000 monomer units, or from about 50 to about 2,500 monomer units.

Some polymers cannot adhere to metal surfaces. For a polymer that does not have any inherent adhesion to metal surfaces, a primer of that pure polymer may have to be used to achieve optimum adhesion to metal stents.

To improve adhesion of the inventive copolymer to metal surfaces, at least one dihydroxyaryl group could be conjugated to the ends of the copolymer. The dihydroxyaryl group(s) can contain a dihydroxyphenyl moiety. Ortho-dihydroxyphenyl groups in 3,4-dihydroxyphenyl alanine have been shown to be responsible for the bonding of mussel adhesive proteins to a variety of metallic substrates. B. P. Lee et al., *Biomacromolecules*, 3: 1038-1047 (2002). Other 3,4-dihydroxyphenyl-containing compounds that can be conjugated to the ends of the copolymer to increase its adhesion to metal surfaces include, e.g., dopamine and 3,4-dihydroxyhydrocinnamic acid.

Accordingly, in some embodiments, optionally in combination with one or more other embodiments described herein, at least one dihydroxyaryl group is conjugated to the ends of the inventive copolymer. In an embodiment, the at least one dihydroxyaryl group contains an ortho-dihydroxyphenyl moiety. In one embodiment, the at least one dihydroxyaryl group contains a 1,2-dihydroxyphenyl moiety. In another embodiment, the at least one dihydroxyaryl group contains a 3,4-dihydroxyphenyl moiety. 3,4-Dihydroxyphenyl-containing compounds that could be conjugated to the ends of the copolymer include, e.g., dopamine and 3,4-dihydroxyhydrocinnamic acid.

Copolymer Containing Blocks or Segments

The copolymer of the invention can also be configured to contain one or more blocks or segments. In certain embodiments, optionally in combination with one or more other embodiments described herein, the copolymer is composed of two blocks or segments, or three blocks or segments, or four blocks or segments, or five blocks or segments. Certain blocks or segments can be the same as one another or different than other blocks or segments. The monomer components can be arranged in any manner (e.g., block, graft, random, alternating, etc.) within each of the blocks or segments.

In some embodiments, optionally in combination with one or more other embodiments described herein, at least one of the blocks or segments of the copolymer is derived from dioxanone, and each of the blocks or segments is independently derived from one to four different types of monomer selected from dioxanone, ester-based monomers, carbonate-based monomers, ether-based monomers or a combination thereof. In one embodiment, optionally in combination with one or more other embodiments described herein, each type of monomer in a block or segment has from about 5 to about 5,000 monomer units. In narrower embodiments, each type of monomer in a block or segment independently has from about 10 to about 4,500 monomer units, or from about 20 to about 4,000 monomer units, or from about 30 to about 3,500 monomer units, or from about 40 to about 3,000 monomer units, or from about 50 to about 2,500 monomer units.

The mechanical properties (e.g., strength, rigidity, toughness and flexibility) and physical properties (e.g., $T_g/T_m$, crystallinity, degradation rate and drug permeability) of a copolymer containing one or more blocks or segments can be tuned by appropriate selection of monomer components; the number, ratio, and arrangement of the monomer components; the length or molecular weight, weight ratio, and arrangement of the blocks or segments; and any other substances physically or chemically attached to, blended with, or incorporated with the copolymer.

For greater strength and rigidity and a higher $T_g/T_m$, a particular block or segment can be enriched in certain types of monomers, e.g., GA, DLA, LLA, DLLA or a combination thereof. Likewise, for greater toughness and flexibility and a lower $T_g/T_m$, a particular block or segment can contain a greater ratio of other types of monomers, e.g., DS, CL, TMC, propiolactone, valerolactone, acetal or a combination thereof. Similarly, the degradation rate of a particular block or segment can be enhanced if it is enriched in certain types of monomers, e.g., DS, GA, DLA, LLA, DLLA or a combination thereof.

To provide greater strength and rigidity, one or more blocks or segments of the copolymer can be formulated to have a higher $T_g$ or $T_m$. In a specific embodiment, the "harder" block or segment has a $T_g$ or $T_m$ above body temperature. In certain embodiments, optionally in combination with one or more other embodiments described herein, the $T_g$ or $T_m$ of the harder block or segment ranges from about 30° C. to about 300° C., or from about 40° C. to about 250° C., or from about 50° C. to about 200° C., or from about 60° C. to about 150° C., or from about 70° C. to about 100° C.

To increase fracture toughness, flexibility, degradation rate and drug permeability, one or more blocks or segments of the copolymer can be designed to have a lower $T_g$ or $T_m$. The "softer" block or segment has a $T_g$ or $T_m$ less than the $T_g$ or $T_m$ of the harder block or segment. In some embodiments, optionally in combination with one or more other embodiments described herein, the $T_g$ of the softer block or segment ranges from about −200° C. to about 100° C., or from about −150° C. to about 75° C., or from about −100° C. to about 50° C., or from about −50° C. to about 30° C., or from about −20° C. to about 10° C. In a particular embodiment, the softer block or segment has a $T_g$ below body temperature. It should be understood that in some cases, the softer block or segment may have a $T_m$ rather than a $T_g$, and the scope of the present invention encompasses cases where the softer block or segment has a $T_m$ rather than a $T_g$.

The blocks or segments of the copolymer may or may not be miscible with each other. In one embodiment, the blocks or segments are partially or completely miscible with each other. In another embodiment, the blocks or segments are partially or completely immiscible with one another.

For the blocks or segments to form discrete phases which are indicative of an immiscible system, they need to be of a certain minimal size. When a two-phase system forms, each phase is saturated with the other phase, although these saturated concentrations may be very small. Accordingly, in some embodiments, the blocks or segments of the copolymer each independently have an $M_n$ of at least about 1 kDa, or at least about 5 kDa, or at least about 10 kDa. In certain embodiments, optionally in combination with one or more other embodiments described herein, the blocks or segments each independently range in $M_n$ from about 1 kDa to about 500 kDa, or from about 5 kDa to about 450 kDa, or from about 10 kDa to about 400 kDa, or from about 20 kDa to about 300 kDa, or from about 30 kDa to about 200 kDa, or from about 40 kDa to about 100 kDa.

In further embodiments, optionally in combination with one or more other embodiments described herein, the ratio of the molecular weight of a harder block or segment to a softer block or segment is between about 20:1 and about 1:20, or between about 15:1 and about 1:15, or between about 10:1 and about 1:10, or between about 5:1 and about 1:5, or between about 2:1 and 1:2.

In other embodiments, optionally in combination with one or more other embodiments described herein, the weight fraction of a harder block with respect to the total copolymer is from about 1% to about 99%, or from about 10% to about 90%, or from about 20% to about 80%, or from about 30% to about 70%, or from about 40% to about 60%. In yet other embodiments, the copolymer can contain about 1-50 wt %, or about 5-40 wt %, or about 10-30 wt % of a harder block or segment, and about 50-99% wt %, or about 60-95 wt %, or about 70-90 wt %, respectively, of a softer block or segment.

Biocompatible Moieties

Besides increasing toughness, flexibility, degradation rate and drug permeability, dioxanone enhances the biocompatibility of a copolymer composed of DS units. For example, a PDS-based suture elicits little or no foreign body reaction (i.e., immune response) to it, and is more biocompatible than a PGA-based suture.

To further improve its biocompatibility, the inventive copolymer can comprise at least one additional biologically compatible ("biocompatible") moiety. Accordingly, in some embodiments, optionally in combination with one or more other embodiments described herein, the inventive composition comprises the biodegradable, dioxanone-based copolymer and at least one additional biocompatible moiety. The at least one additional biocompatible moiety can be physically or chemically attached to, blended with, or incorporated with the copolymer. The at least one additional biocompatible moiety can be selected in such a way as to adjust the biodegradability of the copolymer (e.g., to make the entire copolymer biologically degradable).

Examples of suitable biocompatible moieties include, but are not limited to, poly(alkylene glycols), e.g., poly(ethylene glycol) (PEG), poly(ethylene oxide), poly(propylene glycol) (PPG), poly(tetramethylene glycol) and poly(ethylene oxide-co-propylene oxide); lactones and lactides, e.g., ε-caprolactone, β-butyrolactone, δ-valerolactone and glycolide; poly (N-vinyl pyrrolidone); poly(acrylamide methyl propane sulfonic acid) and salts thereof (AMPS and salts thereof); poly(styrene sulfonate); sulfonated dextran; polyphosphazenes; poly(orthoesters); poly(tyrosine carbonate); sialic acid; hyaluronic acid; hyaluronic acid having a stearoyl or palmitoyl substitutent group; copolymers of PEG with hyaluronic acid, hyaluronic acid-stearoyl or hyaluronic acid-palmitoyl; heparin; copolymers of PEG with heparin; a graft copolymer of poly(L-lysine) and PEG; and copolymers thereof. To ensure its renal clearance, the molecular weight of a polymeric biocompatible moiety may be 40 kDa or less, e.g., between about 300 and about 40,000 Daltons, or between about 8,000 and about 30,000 Daltons, e.g., about 15,000 Daltons.

In one embodiment, optionally in combination with one or more other embodiments described herein, the at least one additional biocompatible moiety is selected from poly(ethylene oxide), poly(propylene glycol), poly(tetramethylene glycol), poly(ethylene oxide-co-propylene oxide), ε-caprolactone, β-butyrolactone, δ-valerolactone, glycolide, poly(N-vinyl pyrrolidone), poly(acrylamide methyl propane sulfonic acid) and salts thereof, poly(styrene sulfonate), sulfonated dextran, polyphosphazenes, poly(orthoesters), poly(tyrosine carbonate), sialic acid, hyaluronic acid and derivatives thereof, copolymers of poly(ethylene glycol) (PEG) with hyaluronic acid or derivatives thereof, heparin, copolymers of PEG with heparin, graft copolymers of poly(L-lysine) and PEG, and copolymers thereof.

In some embodiments, optionally in combination with one or more other embodiments described herein, the at least one additional biocompatible moiety specifically cannot be one or more of any of the biocompatible moieties described herein.

Non-Fouling Moieties

The body's reaction to foreign material could lead to adsorption of proteins on the surface of an implantable device, which could ultimately impair the device's functioning and result in adverse side effects such as thrombosis. A non-fouling moiety provides an implantable device with the ability to resist protein adsorption on its surface. Accordingly, some embodiments of the inventive composition, optionally in combination with one or more other embodiments described herein, comprise the biodegradable, dioxanone-based copolymer and at least one non-fouling moiety. The at least one non-fouling moiety can be physically or chemically attached to, blended with, or incorporated with the copolymer.

Examples of non-fouling moieties include, without limitation, poly(ethylene glycol) (PEG), poly(propylene glycol), polyethylene oxide, PLURONIC™ surfactants (polypropylene oxide-co-PEG), PEO-PPO surfactants (PLURONIC™ polyols, poly(ethylene oxide-co-propylene oxide)), poly(tetramethylene glycol), amino-terminated PEG, hydroxy functionalized poly(vinyl pyrrolidone), dextran, dextrin, sulfonated dextran, dermatan sulfate, silk-elastin block copolymers, sodium hyaluronate, hyaluronic acid, poly(2- hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP) (e.g., R7), phosphoryl choline, heparin, chondroitan sulfate, glycosaminoglycans, chitosan, and derivatives thereof.

Silk and elastin both are natural proteins. Silk possesses great strength and elastin high flexibility. Their combination in a block copolymer makes the non-fouling moiety very strong and, at the same time, very flexible. Silk-elastin block-copolymer can be obtained from Protein Polymer Technologies, Inc. of San Diego, Calif.

In a specific embodiment, optionally in combination with one or more other embodiments described herein, the at least one non-fouling moiety is selected from polyethylene glycol (PEG), polypropylene glycol, PLURONIC™ surfactants (polypropylene oxide-co-PEG), poly(2-hydroxyethyl methacrylate) (PHEMA), poly(vinyl alcohol) (PVA), polyalkene oxides, poly(n-propylmethacrylamide), poly(N-vinyl-2-pyrrolidone) (PVP), sulfonated polystyrene, dextran, sulfonated dextran, dextrin, hyaluronic acid, sodium hyaluronate, and derivatives thereof.

In some embodiments, optionally in combination with one or more other embodiments described herein, the at least one non-fouling moiety specifically cannot be one or more of any of the non-fouling moieties described herein.

The maximum molecular weight of the at least one non-fouling moiety or, if the non-fouling moiety itself is biodegradable, the maximum molecular weight of the largest fragment formed should be low enough so that it is small enough to pass through the kidneys of an animal (e.g., a human). Thus, in certain embodiments, the molecular weight of the non-fouling moiety or its largest fragment is 40 kDa or less, or 30 kDa or less, or 20 kDa or less.

Biobeneficial Materials

To improve the biological properties of an implantable device (e.g., enhance its biocompatibility and reduce protein adsorption on its surface), the device can be formed of a material comprising a biobeneficial material. Therefore, some embodiments of the inventive composition, optionally in combination with one or more other embodiments described herein, comprise the biodegradable, dioxanone-based copolymer and at least one biobeneficial material. The biobeneficial material may be a polymeric material or a non-polymeric material, and may be biodegradable or non-degradable. In certain embodiments, the at least one biobeneficial material is flexible, biodegradable, biocompatible, non-toxic, non-antigenic and/or non-immunogenic. The biobeneficial material can be physically or chemically attached to, blended with, or incorporated with the copolymer.

The biobeneficial material, if polymeric, may have a relatively low $T_g$, e.g., a $T_g$ less than or significantly less than that of the inventive copolymer. In an embodiment, the $T_g$ of the biobeneficial material is below body temperature. Having a $T_g$ below or significantly below that of the copolymer, the biobeneficial material would be relatively soft as compared to the copolymer. This attribute would, e.g., allow a layer of coating containing the biobeneficial material to fill any surface damages that may arise with an implantable device coated with a layer comprising the copolymer. For example, during radial expansion of a stent, a more rigid copolymer can crack or have surface fractures. A softer biobeneficial material can fill in the crack and fractures.

The biobeneficial material can also be hydrophlic. Hydrophicility of, e.g., the coating material would affect the drug-release rate of a drug-delivery coating and, if the coating material is biodegradable, would affect the degradation rate of the coating material. Generally, the more hydrophilic the coating material, the greater the drug-release rate of the drug-delivery coating and the greater the degradation rate of the coating if it is biodegradable.

Examples of biobeneficial materials include, but are not limited to, polyethers (e.g., poly(ethylene glycol) (PEG)); poly(ether esters); co-poly(ether-esters) (e.g. PEO/PLA); polyalkylene oxides (e.g., poly(ethylene oxide) and poly(propylene oxide)); polyalkylene oxalates; polyphosphazenes; phosphoryl choline; choline; poly(aspirin); polymers and copolymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP); carboxylic acid bearing monomers such as methacrylic acid (MA), acrylic acid (AA), alkoxymethacrylate, alkoxyacrylate, and 3-trimethylsilylpropyl methacrylate (TMSPMA); copolymers of PEG such as poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), and poly(vinylidene fluoride)-PEG (PVDF-PEG); PLURONIC™ surfactants (polypropylene oxide-co-polyethylene glycol); poly (tetramethylene glycol); biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharides, elastin, chitosan, and alginate; silicones; and combinations and copolymers thereof.

In certain embodiments, optionally in combination with one or more other embodiments described herein, the at least one biobeneficial material is selected from fibrin; fibrinogen; cellulose and cellulose derivatives (e.g., cellulose acetate, cellulose butyrate, cellulose acetate butyrate, cellophane, cellulose nitrate, cellulose propionate, cellulose ethers, and carboxymethyl cellulose); starch; pectin; chitosan; elastin; gelatin; alginate and conjugates thereof (e.g., alginate-gelatin, alginate-collagen, alginate-laminin, alginate-elastin, alginate-collagen-laminin and alginate-hyaluronic acid); collagen and conjugates thereof; hyaluronan and derivatives thereof (e.g., methacrylate-modified hyaluronan and NHS ester-modified hyaluronan); hyaluronic acid; sodium hyaluronate; and self-assembled peptides (SAP) (e.g., Ac-RARADADARARADADA-NH, (SEQ ID NO. 1) (RAD 16-II), VKVKVKVKV-PP-TKVKVKVKV-NH$_2$ (SEQ ID NO. 2) (MAX-1), and Ac-AEAEAKAKAEAEAKAK-NH, (SEQ ID NO. 3) (EAK 16-II)).

In another embodiment, the biobeneficial material is a block copolymer having flexible poly(ethylene glycol) and poly(butylene terephthalate) blocks (PEG/PBT) (e.g., POLYACTIVE™). POLYACTIVE™ is intended to include AB, ABA, and BAB copolymers having such segments of PEG and PBT (e.g., poly(ethylene glycol)-block-poly(butylene terephthalate)-block-poly(ethylene glycol) (PEG-PBT-PEG)).

In some embodiments, optionally in combination with one or more other embodiments described herein, the at least one biobeneficial material specifically cannot be one or more of any of the biobeneficial materials described herein.

Biologically Active Agents

Further embodiments of the invention, optionally in combination with one or more other embodiments described herein, are directed to a composition comprising the biodegradable, dioxanone-based copolymer and at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the inventive composition comprises at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopforen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammmatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., TAXOTERE® from Aventis), methotrexate, azathioprine, vincristine, vinblastine, fluorouracil, doxorubicin hydrochloride (e.g., ADRIAMYCIN® from Pfizer), and mitomycin (e.g., MUTAMYCIN® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name MEVACOR® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., CAPOTEN® and CAPOZIDE® from Bristol-Myers Squibb), cilazapril and lisinopril (e.g., PRINIVIL® and PRINZIDE® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO).

Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A:10-19 (2004). Endothelial cells can be selectively targeted (for the targeted delivery of immunoliposomes) using scFv A5. T. Volkel, et al., *Biochimica et Biophysica Acta*, 1663:158-166 (2004). Junction membrane protein vascular endothelial (VE)-cadherin has been shown to bind to endothelial cells and down regulate apoptosis of the endothelial cells. R. Spagnuolo, et al., *Blood*, 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Trp-Gly (SEQ ID NO:4)). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the composition of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, pro-drugs thereof, co-drugs thereof, and a combination thereof. In a particular embodiment, the bioactive agent is everolimus. In another specific embodiment, the bioactive agent is clobetasol.

In some embodiments, optionally in combination with one or more other embodiments described herein, the at least one biologically active agent specifically cannot be one or more of any of the bioactive drugs or agents described herein.

Material and Coating

The inventive composition comprising the biodegradable, dioxanone-based copolymer can be used to make a material of which an implantable device is formed. Such a material can comprise any combination of embodiments of the inventive composition described herein.

Accordingly, some embodiments of the invention, optionally in combination with one or more other embodiments described herein, are drawn to a material containing any combination of embodiments of the composition comprising the biodegradable, dioxanone-based copolymer. For example, the composition forming the material can optionally have at least one dihydroxyaryl group conjugated to the ends of the copolymer and can optionally contain at least one additional biocompatible moiety, at least one non-fouling moiety, at least one biobeneficial material, at least one biologically active agent, or a combination thereof.

The material of the invention can be used to make a portion of an implantable device or the whole device itself. For example, the material can be used to make a coating that is disposed over at least a portion of the device.

Accordingly, some embodiments of the invention, optionally in combination with one or more other embodiments described herein, are directed to a coating containing any combination of embodiments of the composition comprising the biodegradable, dioxanone-based copolymer. For example, the composition forming the coating can optionally have at least one dihydroxyaryl group conjugated to the ends of the copolymer and can optionally contain at least one additional biocompatible moiety, at least one non-fouling moiety, at least one biobeneficial material, at least one biologically active agent, or a combination thereof.

The coating can have a range of thickness and degradation rates. In some embodiments, optionally in combination with one or more other embodiments described herein, the coating has a thickness of about 30 micron, or about 20 micron, or ≤ about 10 micron, or about 5 micron. In further embodiments, optionally in combination with one or more other embodiments described herein, the coating completely or substantially completely degrades within about 24 months, or within about 18 months, or within about 12 months, or within about 6 months, or within about 3 months, or within about 2 months, or within about 1 month (i.e., 30 days).

Implantable Device

The inventive material containing any combination of embodiments of the composition comprising the biodegradable, dioxanone-based copolymer can be used to form an implantable device. Accordingly, some embodiments of the invention, optionally in combination with one or more other embodiments described herein, are drawn to an implantable device formed of a material containing any combination of embodiments of the composition comprising the biodegradable, dioxanone-based copolymer. For example, the implantable device can be formed of a material comprising a composition that can optionally have at least one dihydroxyaryl group conjugated to the ends of the copolymer and can optionally contain at least one additional biocompatible moiety, at least one non-fouling moiety, at least one biobeneficial material, at least one biologically active agent, or a combination thereof.

A portion of the implantable device or the whole device itself can be formed of the material containing any combination of embodiments of the composition comprising the biodegradable, dioxanone-based copolymer. For example, a coating containing any combination of embodiments of the composition comprising the biodegradable, dioxanone-based copolymer can be disposed over at least a portion of the implantable device.

Accordingly, certain embodiments of the invention, optionally in combination with one or more other embodiments described herein, are directed to an implantable device formed of a coating containing any combination of embodiments of the composition comprising the biodegradable, dioxanone-based copolymer. The coating is disposed over at least a portion of the device. For example, the implantable device can be formed of a coating comprising a composition that can optionally have at least one dihydroxyaryl group conjugated to the ends of the copolymer and can optionally contain at least one additional biocompatible moiety, at least one non-fouling moiety, at least one biobeneficial material, at least one biologically active agent, or a combination thereof.

The implantable device can be formed of a coating that can have a range of thickness and degradation rates. In some embodiments, optionally in combination with one or more other embodiments described herein, the implantable device is formed of a coating that has a thickness of about 30 micron, or about 20 micron, or about 10 micron, or ≤ about 5 micron. In further embodiments, optionally in combination with one or more other embodiments described herein, the implantable device is formed of a coating that completely or substantially completely degrades within about 24 months, or within about 18 months, or within about 12 months, or within about 6 months, or within about 3 months, or within about 2 months, or within about 1 month (i.e., 30 days).

The present invention also encompasses implantable devices formed of bioabsorbable polymers, biostable polymers, or a combination thereof. In some embodiments, optionally in combination with one or more other embodiments described herein, a portion of the device (e.g., a coating disposed over the device) or the whole device itself can be formed of such polymers and any other substances described herein.

Any implantable device can be formed of the inventive material or coating containing any combination of embodiments of the composition comprising the biodegradable, dioxanone-based copolymer. Non-limiting examples of implantable devices include stents (e.g., coronary stents and peripheral stents), grafts (e.g., aortic grafts, arterio-venous grafts, vascular grafts and by-pass grafts), stent-grafts, catheters, guidewires, leads and electrodes for pacemakers and defibrillators, endocardial leads (e.g., FINELINE and ENDOTAK, available from Abbott Vascular, Santa Clara, Calif.), clips (e.g., anastomotic clips), shunts (e.g., cerebrospinal fluid and axius coronary shunts), closure devices (e.g., arterial and patent foramen ovale closure devices), valves (e.g., artificial heart valves), ventricular assist devices, artificial heart, and blood oxygenators. Furthermore, the inventive material containing any combination of embodiments of the composition comprising the biodegradable copolymer can be used to make other types of substrates including, e.g., nanofibers, sustained-release small molecule or protein formulations, microspheres, and particles (e.g., drug-delivery particles, microparticles and nanoparticles).

In certain embodiments, optionally in combination with one or more other embodiments described herein, the implantable device is selected from stents, grafts, stent-grafts, catheters, leads and electrodes, clips, shunts, closure devices, valves and particles. In a specific embodiment, the implantable device is a stent. The stent may be balloon-expandable or self-expandable. Moreover, the stent can be intended for any vessel in the body, e.g., neurological, carotid, vein graft, synthetic graft, arteriovenous anastamosis, coronary, aortic renal, iliac, femoral, popliteal vasculature and urethral passages.

The underlying structure of the implantable device can be of virtually any design. A portion of the device, or the whole device itself, can be made of a metallic material, an alloy, a polymeric material, any other type of material, or a combination thereof, as is known in the art. For example, a polymeric material comprising any combination of embodiments of the inventive composition can be used to make a portion of the implantable device or the whole device itself.

Non-limiting examples of metallic materials and alloys suitable for fabricating implantable devices include cobalt-chromium alloys (e.g., ELGILOY), "L-605", stainless steel (316L), "MP35N," "MP20N," ELASTINITE (Nitinol), tantalum, tantalum-based alloys, nickel-titanium alloys, platinum, platinum-based alloys (e.g., platinum-iridium alloy), iridium, gold, magnesium, titanium, titanium-based alloys, zirconium-based alloys, or combinations thereof. "L-605" is a trade name for an alloy of cobalt, chromium, tungsten, nickel and iron available as Haynes 25 from Haynes International (Kokomo, Ind.). "L-605" consists of 51% cobalt, 20% chromium, 15% tungsten, 10% nickel and 3% iron. "MP35N" and "MP20N" are trade names for alloys of cobalt, nickel, chromium and molybdenum available from Standard Press Steel Co. (Jenkintown, Pa.). "MP35N" consists of 35% cobalt, 35% nickel, 20% chromium and 10% molybdenum. "MP20N" consists of 50% cobalt, 20% nickel, 20% chromium and 10% molybdenum.

If a polymeric material is used to make a portion (e.g., a coating) of the implantable device or the whole device itself, the polymeric material can comprise any combination of embodiments of the inventive composition, e.g., the biodegradable copolymer of the invention, a blend of different types of polymers, a blend of polymer(s) and additional substance(s), or a combination thereof. Further, additional polymer(s) and/or additional substance(s) can be physically or chemically attached to the underlying copolymer forming the device or a portion thereof. The additional polymer(s) and/or additional substance(s) that can be physically or chemically attached to, blended with, or incorporated with the underlying polymer can include, but are not limited to, biocompatible polymers, bioabsorbable polymers, biocompatible moieties, non-fouling moieties, biobeneficial substances and materials, and bioactive agents. To enhance the mechanical characteristics (e.g., strength and rigidity) of an implantable device made substantially of a polymeric material, the device can be supported by additional structure(s) (e.g., struts in the case of stents made substantially of a polymeric material).

Structure of Coating

According to some embodiments of the invention, optionally in combination with one or more other embodiments described herein, a coating disposed over an implantable device (e.g., a stent) can be a multi-layer structure that can include any of the following four layers or combination thereof:

(1) a primer layer;
(2) a drug-polymer layer (also referred to as a "reservoir" or "reservoir layer") or, alternatively, a polymer-free drug layer;
(3) a topcoat layer; and/or
(4) a finishing coat layer.

Each layer of a stent coating can be disposed over the stent by dissolving the polymer or a blend of polymers in a solvent, or a mixture of solvents, and disposing the resulting polymer solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time between about 5 minutes and about 60 minutes, if desired, to improve the thermodynamic stability of the coating.

To incorporate a bioactive agent (e.g., a drug) into the reservoir layer, the drug can be combined with the polymer solution that is disposed over the stent as described above. Alternatively, if it is desirable to have the stent coating with a fast drug-release rate, a polymer-free reservoir can be made. To fabricate a polymer-free reservoir, the drug can be dissolved in a suitable solvent or mixture of solvents, and the resulting drug solution can be disposed over the stent by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied directly or indirectly over at least a portion of the stent surface to serve as a reservoir for at least one bioactive agent (e.g., drug) that is incorporated into the reservoir layer. The optional primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

The process of the release of a drug from a coating having both topcoat and finishing coat layers includes at least three steps. First, the drug is absorbed by the polymer of the topcoat layer at the drug-polymer layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the blood vessel or surrounding tissue. Consequently, a combination of the topcoat and finishing coat layers, if used, can serve as a rate-limiting barrier. The drug can be released by virtue of the degradation, dissolution, and/or erosion of the layer(s) forming the coating, or via migration of the drug through non-degradable polymeric layer(s) into a blood vessel or tissue.

In one embodiment, any or all of the layers of the stent coating can be made of biologically degradable/erodable/absorbable/resorbable polymer(s), non-degradable/biostable polymer(s), or a combination thereof. In another embodiment, the outermost layer of the coating can be limited to biodegradable polymer(s), biostable polymer(s), or a combination thereof.

To illustrate in more detail, in a stent coating having all four layers described above (i.e., the primer, the reservoir layer, the topcoat layer and the finishing coat layer), the outermost layer is the finishing coat layer, which can be made of biodegradable polymer(s), biostable polymer(s), or a combination thereof. The remaining layers (i.e., the primer, the reservoir layer and the topcoat layer) optionally can also be fabricated of biodegradable polymer(s), biostable polymer(s), or a combination thereof. The polymer(s) in a particular layer may be the same as or different than those in any of the other layers.

If a finishing coat layer is not used, the topcoat layer can be the outermost layer and can be made of biodegradable polymer(s), biostable polymer(s), or a combination thereof. In this case, the remaining layers (i.e., the primer and the reservoir layer) optionally can also be fabricated of biodegradable polymer(s), biostable polymer(s), or a combination thereof. The polymer(s) in a particular layer may be the same as or different than those in any of the other layers.

If neither a finishing coat layer nor a topcoat layer is used, the stent coating could have only two layers—the primer and the reservoir. In such a case, the reservoir is the outermost layer of the stent coating and can be made of biodegradable polymer(s), biostable polymer(s), or a combination thereof. The primer optionally can also be fabricated of biodegradable polymer(s), biostable polymer(s), or a combination thereof. The two layers may be made from the same or different polymers.

Increased rate of degradation, erosion, absorption and/or resorption of biologically degradable, erodable, absorbable and/or resorbable polymer(s) can lead to an increased rate of release of a drug due to the gradual disappearance of the polymer(s) that form the reservoir, the topcoat layer, and/or the finishing coat layer. Through appropriate selection of biodegradable polymer(s), biostable polymer(s) or a combination thereof, a stent coating can be engineered to provide either fast or slow release of a drug, as desired. Those having ordinary skill in the art can determine whether a stent coating having slow or fast drug-release rate is advisable for a particular drug. For example, fast release may be recommended for stent coatings loaded with antimigratory drugs, which often need to be released within 1 to 2 weeks. For anti-proliferative and anti-inflammatory drugs, slower release may be desired, e.g., up to 30-day and 60-day release times, respectively.

Any layer of a stent coating can contain any amount of a bioabsorbable polymer and/or a biocompatible polymer, or a blend of more than one such polymer. Non-limiting examples of bioabsorbable polymers and biocompatible polymers include polyacrylates, e.g., poly(butyl methacrylate), poly(ethyl methacrylate), poly(ethyl methacrylate-co-butyl methacrylate), poly(acrylonitrile), poly(ethylene-co-methyl methacrylate), poly(acrylonitrile-co-styrene) and poly(cyanoacrylates); fluorinated polymers and/or copolymers, e.g., poly(vinylidene fluoride) and poly(vinylidene fluoride-co-hexafluoro propylene); poly(N-vinyl pyrrolidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(ether-esters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose); polyurethanes; silicones; polyesters; polyolefins; polyisobutylene and ethylene-alphaolefin copolymers; vinyl halide polymers and copolymers, e.g., polyvinyl chloride; polyvinyl ethers, e.g., polyvinyl methyl ether; polyvinylidene chloride; polyvinyl ketones; polyvinyl aromatics, e.g., polystyrene; polyvinyl esters, e.g., polyvinyl acetate; copolymers of vinyl monomers with each other and olefins, e.g., poly(ethylene-co-vinyl alcohol) (EVAL); ABS resins; poly(ethylene-co-vinyl acetate); polyamides, e.g., Nylon 66 and polycaprolactam; alkyd resins; polycarbonates; polyoxymethylenes; polyimides; polyethers; epoxy resins; polyurethanes; rayon; rayon-triacetate; and copolymers thereof.

Any layer of a stent coating can also contain any amount of a non-degradable polymer, or a blend of more than one such polymer. Non-limiting examples of non-degradable polymers include methylmethacrylate, ethylmethacrylate, butylmethacrylate, 2-ethylhexylmethacrylate, laurylmethacrylate, hydroxylethyl methacrylate, polyethylene glycol (PEG) acrylate, PEG methacrylate, 2-methacryloyloxyethylphosphorylcholine (MPC) and n-vinyl pyrrolidone, methacrylic acid, acrylic acid, hydroxypropyl methacrylate, hydroxypropylmethacrylamide, 3-trimethylsilylpropyl methacrylate, and copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing any combination of embodiments of the composition comprising the biodegradable, dioxanone-based copolymer. For example, the method comprises forming the implantable device of a material comprising a composition that can optionally have at least one dihydroxyaryl group conjugated to the ends of the copolymer and can optionally contain at least one additional biocompatible moiety, at least one non-fouling moiety, at least one biobeneficial material, at least one biologically active agent, or a combination thereof.

Under the method, a portion of the implantable device or the whole device itself can be formed of the material containing any combination of embodiments of the composition comprising the biodegradable copolymer. For example, the method can comprise depositing over at least a portion of the implantable device a coating containing any combination of embodiments of the composition comprising the biodegradable copolymer.

Accordingly, in one embodiment, the method comprises disposing over at least a portion of an implantable device a coating containing any combination of embodiments of the composition comprising the biodegradable, dioxanone-based copolymer. For example, the method comprises depositing over at least a portion of an implantable device a coating comprising a composition that can optionally have at least one dihydroxyaryl group conjugated to the ends of the copolymer and can optionally contain at least one additional biocompatible moiety, at least one non-fouling moiety, at least one biobeneficial material, at least one biologically active agent, or a combination thereof.

The method can deposit a coating having a range of thickness over an implantable device. In certain embodiments, the method deposits over at least a portion of the implantable device a coating that has a thickness of $\leq$ about 30 micron, or about 20 micron, or about 10 micron, or $\leq$ about 5 micron.

In certain embodiments, the method is used to fabricate an implantable device selected from stents, grafts, stent-grafts, catheters, leads and electrodes, clips, shunts, closure devices, valves, and particles. In a specific embodiment, the method is used to fabricate a stent.

The copolymer of the invention, and any other desired substances and materials, can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus.

Non-limiting examples of polymers that can be used to fabricate an implantable device include poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide), poly(D,L-lactide), poly(caprolactone), poly(trimethylene carbonate), polyethylene amide, polyethylene acrylate, poly(glycolic acid-co-trimethylene carbonate), co-poly (ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Additional representative examples of polymers that may be suited for fabricating an implantable device include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF of Thorofare, N.J.), polyvinylidene fluoride (otherwise known as KYNAR, available from ATOFINA Chemicals of Philadelphia, Pa.), poly(tetrafluoroethylene-co-hexafluoropropylene-co-vinylidene fluoride), ethylene-vinyl acetate copolymers, and polyethylene glycol.

Method of Treating or Preventing Disorders

An implantable device formed of a material or coating containing any combination of embodiments of the composition comprising the biodegradable, dioxanone-based copolymer can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein. For example, the material can be a coating disposed over at least a portion of the device.

Accordingly, some embodiments of the invention, optionally in combination with one or more other embodiments described herein, are drawn to a method of treating, preventing or diagnosing a condition or disorder in a patient, comprising implanting in the patient an implantable device formed of a material or coating containing any combination of embodiments of the composition comprising the biodegradable, dioxanone-based copolymer. For example, the implantable device can be formed of a material or coating comprising a composition that can optionally have at least one dihydroxyaryl group conjugated to the ends of the copolymer and can optionally contain at least one additional biocompatible moiety, at least one non-fouling moiety, at least one biobeneficial material, at least one biologically active agent, or a combination thereof.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material or coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

EXAMPLES

The examples set forth below are shown for the sole purpose of further illustrating embodiments of the present invention and are in no way meant to limit the invention. The following prophetic examples are given to aid in understanding the invention, but it is to be understood that the invention is not limited to the particular materials or procedures of the examples.

Synthesis of Dioxananone-Based Copolymers

The biodegradable, dioxananone-based copolymer of the invention can be prepared by any method of polymerization known in the art. Methods of polymerization include, but are not limited to, solution-based polymerization and melt-phase polymerization. In solution-based polymerization, all the reactive components involved in the polymerization reaction are partially or completely dissolved in a solvent.

The copolymer of the invention can be synthesized by standard methods known to those having ordinary skill in the art, e.g., by ring-opening polymerization (ROP) with the corresponding monomers of the copolymer and using an initiator. ROP can be catalyzed by an organic or inorganic acid (e.g., a Lewis acid), an organic (e.g., a tertiary amine base) or inorganic base (e.g., a Lewis base), an organometallic reagent, and/or heat, if necessary and if compatible with the reactants and product(s) of the reaction. For example, zirconium catalysts such as zirconium acetylacetone, zinc catalysts such as diethylzinc and zinc L-lactate, and tin catalysts such as stannous octoate and tin triflates are particularly suitable for the synthesis of biodegradable polyesters.

In some embodiments, the initiator employed in the synthesis of the copolymer has at least one active end group that is a hydroxyl, amino or thiol group. If the initiator has only one active end group, then the polymer grows only at one end. On the other hand, if the initiator has two active end groups, then a polymerization reaction occurs at both ends of the polymer. In an embodiment, the initiator is a diol, in which one of the hydroxyl end groups may optionally be protected. In another embodiment, the initiator is a diamine, in which one of the amino end groups may optionally be protected. In yet another embodiment, the initiator is a dithiol, in which one of the thiol end groups may optionally be protected. In further embodiments, the dihydroxy, diamino or dithiol initiator is $C_2$-$C_{24}$ and contains an optionally substituted aliphatic, heteroaliphatic, cycloaliphatic, heterocycloaliphatic, aromatic or heteroaromatic group, or a combination thereof. In other embodiments, the initiator is a diol selected from 1,2-ethanediol, 1,3-propanediol, 1,4-butanediol, 1,5-pentanediol, 1,6-hexanediol, 1,7-heptanediol, 1,8-octanediol, diethylene glycol, triethylene glycol, tetraethylene glycol, poly(ethylene glycol), poly(propylene glycol), poly(tetramethylene glycol), and poly(caprolactone)diol.

Accordingly, some embodiments of the invention are directed to a method of preparing the inventive composition, comprising performing ring-opening polymerization (ROP) reactions with an initiator, dioxanone and at least one additional ester-, carbonate- or ether-based monomer, wherein:

the initiator has one or two active hydroxyl, amino or thiol end groups;

the initiator can do the initial ROP reaction with dioxanone or a different ester-, carbonate- or ether-based monomer;

the ROP reaction with each different type of monomer can occur in any order and for any number of times; and a particular ROP reaction can occur in the presence of only one type of monomer or in the presence of two or more different types of monomers.

The various embodiments of the inventive composition comprising the biodegradable, dioxanone-based copolymer can be prepared by optionally:

conjugating at least one dihydroxyaryl group to the ends of the copolymer;

blending or physically or chemically attaching at least one additional biocompatible moiety with or to the copolymer;

blending or physically or chemically attaching at least one non-fouling moiety with or to the copolymer;

blending or physically or chemically attaching at least one biobeneficial material with or to the copolymer; and/or incorporating at least one biologically active agent with the copolymer.

One example of the synthesis of a biodegradable, dioxanone-based copolymer of the invention is the synthesis of P(DS-GA-DLLA-TMC) via ROP in Scheme 1. In this example, mono-protected 1,6-hexanediol is the initiator. It initiates ROP with dioxanone (DS) to form PDS. The hydroxyl end group of PDS then initiates ROP with glycolide (GA) to generate P(DS-GA). Similarly, the hydroxyl end group of P(DS-GA) in turn initiates ROP with D,L-lactide (DLLA) to furnish P(DS-GA-DLLA). Finally, the hydroxyl end group of P(DS-GA-DLLA) initiates ROP with trimethylene carbonate (TMC) to produce P(DS-GA-DLLA-TMC).

In the example illustrated in Scheme 1, it should be understood that a particular ROP reaction with a particular type of monomer can occur any number of times. Therefore, the variables m, n, p and q can be any integer $\geq 1$. For example, each of these variables can independently be 1 to 10,000, or 5 to 5,000, or 10 to 4,000, or 20 to 3,000, or 30 to 2,000, or 40 to 1,000, or 50 to 500. The order of ROP reactions depicted in Scheme 1 is merely illustrative. The ROP reactions involving the four different types of monomer can occur in any order. Moreover, a particular ROP reaction can be random by being performed in the presence of two or more different types of monomers.

If a particular ROP reaction with a particular type of monomer occurs multiple times, a block or segment derived from that monomer can be created. The block or segment can be a certain length or molecular weight, and can alternate with another block or segment derived from another type of monomer. Further, a block or segment can be derived from two or more different types of monomers, wherein each type of monomer undergoes a particular ROP reaction a certain number of times. These ROP reactions can also alternate in forming a block or segment. In addition, a random block or segment can be created by conducting an ROP reaction in the presence of two or more different types of polymers any number of times, optionally conducting another ROP reaction in the presence of two or more other types of polymers any number of times, and so on.

If desired, the protected "left" end of the copolymer in Scheme 1 can remain protected after the polymerization reactions have been completed, and the hydroxyl group at the "right" end can be functionalized in any desired manner. Alternatively, deprotection of the left end of the copolymer allows this end to be functionalized in any desired fashion, with appropriate pre-protection of the right end group, if desired. The use of protecting (or blocking) groups in organic synthesis is well known in the art.

For example, both hydroxyl end groups can be conjugated to a dihydroxyaryl group to enhance the adhesion of the copolymer to metal surfaces. The at least one dihydroxyaryl group can contain, e.g., an ortho-dihydroxyphenyl moiety such as 1,2-dihydroxyphenyl and 3,4-dihydroxyphenyl. 3,4-Dihydroxyphenyl-containing compounds include, e.g., dopamine and 3,4-dihydroxyhydrocinnamic acid. Dopamine could be conjugated to the hydroxyl end groups of the copolymer via coupling with 1,1'-carbonyldiimidazole. 3,4-Dihydroxy-hydrocinnamic acid could be conjugated to the hydroxyl end groups by conversion of the cinnamic acid to the N-succidimyl ester or by use of dicyclohexylcarbodiimide (DCC) and 4-(dimethylamino)pyridinium (DPTS). Alternatively, conjugation of the cinnamic acid could be effected via a Mitsunobu reaction using triphenylphosphine and diethyl azodicarboxylate (DEAD) or diisopropyl azodicarboxylate (DIAD). Conjugation of a dihydroxyaryl group to an active end group (e.g., a hydroxyl, amino or thiol group) could also be effected using other reagents and methods, as is known in the art.

As another example, either the left or the right hydroxyl end group, or both end groups, independently can be attached to a biocompatible moiety, a non-fouling moiety, a biobeneficial material, and/or a bioactive agent. Alternatively, monomers different than those shown in Scheme 1 and bearing a protected side group can be used in synthesizing the copolymer. After completion of the polymerization reactions, the side groups can be deprotected and functionalized as desired, e.g., by attaching them to a biocompatible moiety, a non-fouling moiety, a biobeneficial material, and/or a bioactive agent.

Protection of the right end of the copolymer in Scheme 1 and deprotection of the left end permit the left end to be elaborated in further polymerization reactions. The polymerization reactions occurring at the left end can involve any types of monomers, can transpire any number of times, and can occur in any order and manner, as desired. Alternatively, the 1,6-hexanediol initiator in Scheme 1 can initiate ROP as an unprotected diol. In this case, both the right and left ends of the polymer would be elaborated in the same way in the polymerization reactions.

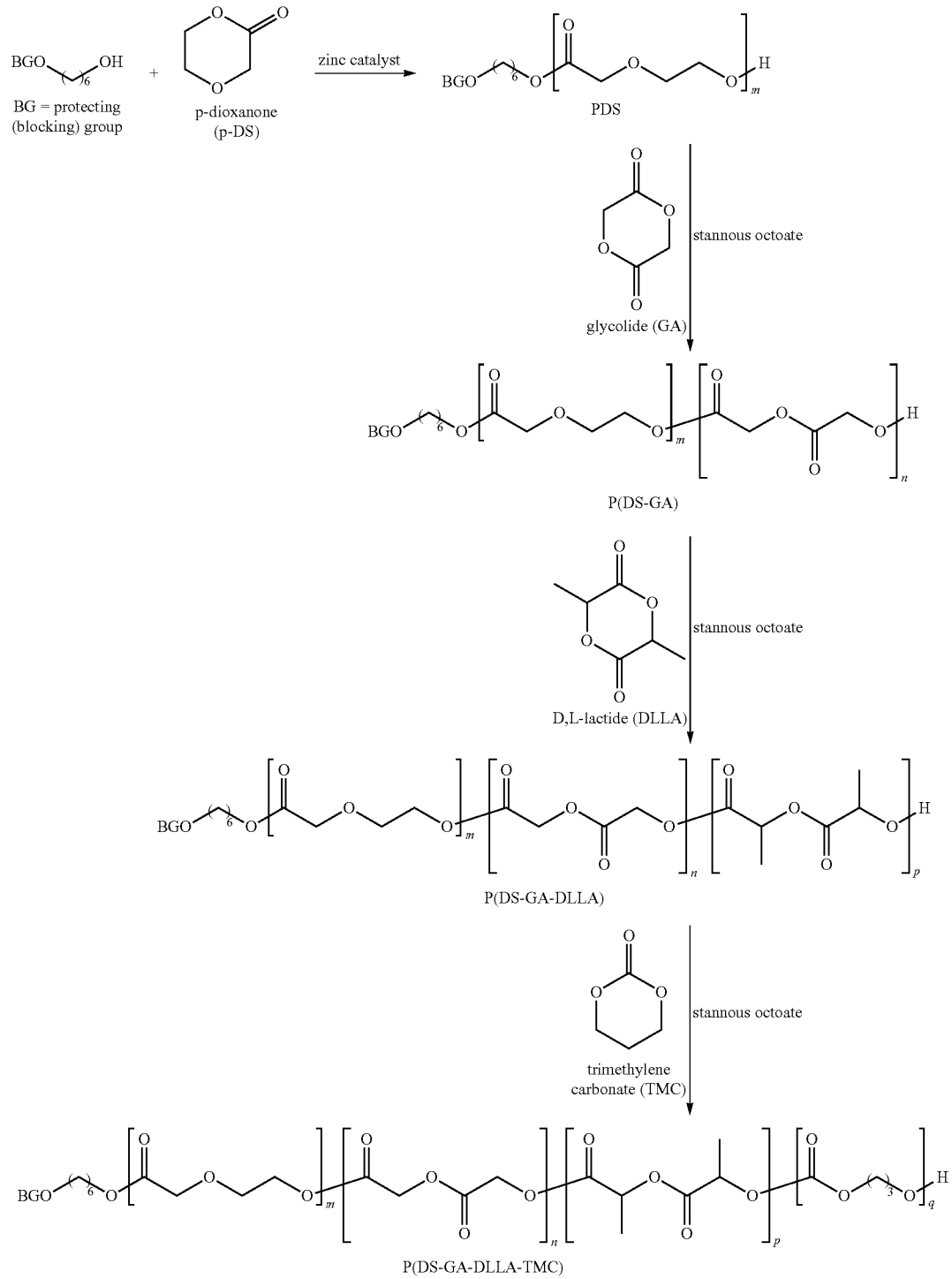

Drug-Coated Stent

The copolymer illustrated in Scheme 1 is dissolved in hexafluoroisopropanol at 2% w/w. Everolimus is added to the solution at a drug-to-polymer ratio of 1:1. Vision stent at 3×18 mm is mounted on a mandrel. The solution is spray-coated on the stent with multiple passes. The solvent is then removed by baking the stent at 50° C. for 2 hours.

While particular embodiments of the present invention have been shown and described, it will be obvious to those skilled in the art that changes and modifications can be made thereto without departing from the invention in its broader aspects. Therefore, the appended claims are to encompass within their scope all such changes and modifications as fall within the true spirit and scope of the present invention.

It should be understood that if a substance can have more than one stereochemistry and/or regiochemistry at one or more stereocenters and/or regiocenters and the stereochemistry and/or regiochemistry of the substance at the one or more stereocenters and/or regiocenters are not indicated, the scope of the present invention encompasses all possible stereoisomers (e.g., enantiomers, diastereomers, etc.) and/or regioisomers of that substance.

What is claimed is:

1. A composition comprising a biodegradable copolymer, wherein the biodegradable copolymer:
is polymerized from dioxanone and three additional different ester-, carbonate- or ether based monomers;
has a crystallinity of about 80% or less;
has a glass transition temperature, $T_g$ from about $-100°$ C. to about $100°$ C.;
has a polymer number-average molecular weight ($M_n$) from about 10 kDa to about 1,500 kDa; and
completely or substantially completely degrades within about 24 months when exposed to physiological conditions;
wherein the additional ester-, carbonate- or ether-based monomers are selected from glycolide (GA), D-lactide (DLA), L-lactide (LLA), D,L-lactide (DLLA), α-bromo-γ-butyrolactone, α-bromo-γ-valerolactone, homoserine lactone $C_2$-$C_{14}$ amide, mevalonolactone, 1,3-dioxolan-2-one, 4-methyl-1,3-dioxolan-2-one, 4-methoxymethyl-1,3-dioxolan-2-one, 4-chloro-1,3-dioxolan-2-one, 4-phenyl-1,3-dioxolan-2-one, 4-vinyl-1,3-dioxolan-2-one, trimethylene carbonate (TMC), β-propiolactone (PL), β-butyrolactone (BL), δ-valerolactone (VL), ε-caprolactone (CL), and propylene oxide (PPO); and
wherein the biodegradable copolymer is a block copolymer comprising four blocks, wherein at least one of the blocks is derived from dioxanone and each of the blocks is independently derived from four different types of monomers selected from dioxanone, the ester-, carbonate-, and ether-based monomers, and each type of monomer in a block has from about 5 to about 5,000 monomer units.

2. The composition of claim 1, wherein the copolymer:
has a crystallinity from about 5% to about 70%;
has a $T_g$ from about $-60°$ C. to about $60°$ C.;
has an $M_n$ from about 20 kDa to about 1,000 kDa; and
completely or substantially completely degrades within about 12 months when exposed to physiological conditions.

3. The composition of claim 1, wherein the copolymer:
has a crystallinity from about 10% to about 60%;
has a $T_g$ from about $-30°$ C. to about $30°$ C.;
has an $M_n$ from about 30 kDa to about 700 kDa; and
completely or substantially completely degrades within about 6 months when exposed to physiological conditions.

4. The composition of claim 1, wherein dioxanone and the additional ester-, carbonate- or ether-based monomers each independently have from about 5 to about 5,000 monomer units.

5. The composition of claim 1, wherein the copolymer is selected from P(DS-GA-DLLA-CL), P(DS-GA-DLLA-TMC), P(DS-GA-CL-TMC), and P(DS-DLLA-CL-TMC).

6. The composition of claim 1, further comprising at least one additional biocompatible moiety selected from poly(ethylene oxide), polypropylene glycol), poly(tetramethylene glycol), poly(ethylene oxide-co-propylene oxide), ε-caprolactone, γ-butyrolactone, δ-valerolactone, glycolide, poly(N-vinyl pyrrolidone), poly(acrylamide methyl propane sulfonic acid) and salts thereof, poly(styrene sulfonate), sulfonated dextran, polyphosphazenes, poly(orthoesters), poly(tyrosine carbonate), sialic acid, hyaluronic acid, copolymers of poly (ethylene glycol) (PEG) with hyaluronic acid, heparin, copolymers of PEG with heparin, graft copolymers of poly (L-lysine) and PEG, and copolymers thereof.

7. The composition of claim 1, further comprising at least one non-fouling moiety selected from polyethylene glycol, polypropylene glycol, polypropylene oxide-co-PEG, poly(2-hydroxyethyl methacrylate), poly(vinyl alcohol), polyalkene oxides, poly(n-propylmethacrylamide), poly(N-vinyl-2-pyrrolidone), sulfonated polystyrene, dextran, sulfonated dextran, dextrin, hyaluronic acid, and sodium hyaluronate.

8. The composition of claim 1, further comprising at least one biobeneficial material selected from fibrin, fibrinogen, cellulose, starch, pectin, chitosan, elastin, gelatin, alginate and conjugates thereof, collagen and conjugates thereof, hyaluronan, hyaluronic acid, and sodium hyaluronate.

9. The composition of claim 1, further comprising at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, and a combination thereof.

10. A coating of an implantable device comprising the composition of claim 1.

11. The coating of claim 10, which has a thickness of ≤ about 10 micron and completely or substantially completely degrades within about 12 months when exposed to physiological conditions.

12. A coating of an implantable device comprising the composition of claim 6.

13. A coating of an implantable device comprising the composition of claim 7.

14. A coating of an implantable device comprising the composition of claim 8.

15. A coating of an implantable device comprising the composition of claim 9.

16. An implantable device formed of a material comprising the composition of claim 1.

17. The device of claim 16, wherein the material is a coating disposed over at least a portion of the device.

18. The device of claim 17, wherein the coating has a thickness of ≤ about 10 micron and completely or substantially completely degrades within about 12 months.

19. The device of claim 16, which is selected from stents, grafts, stent-grafts, catheters, leads and electrodes, clips, shunts, closure devices, valves, and particles.

20. The device of claim 19, which is a stent.

21. An implantable device formed of a material comprising the composition of claim 6.

22. An implantable device formed of a material comprising the composition of claim 7.

23. An implantable device formed of a material comprising the composition of claim 8.

24. An implantable device formed of a material comprising the composition of claim 9.

25. The composition of claim 1, wherein each type of monomer in a block has from about 50 to about 2,500 monomer units.

26. A method of preparing the composition of claim 1, comprising performing ring-opening polymerization (ROP) reactions with an initiator, dioxanone and three additional different ester-, carbonate-, or ether-based monomers, wherein the initiator has one or two active hydroxyl, amino, or thio end groups.

27. A method of fabricating an implantable device, comprising forming the device of a material comprising the composition of claim 1.

28. The method of claim 27, comprising depositing the material as a coating over at least a portion of the implantable device.

29. A method of treating or preventing a condition or disorder in a patient, comprising implanting in the patient an implantable device formed of a material comprising the composition of claim 1, wherein the condition or disorder is selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction.

30. The method of claim 29, wherein the composition further comprises at least one additional biocompatible moiety.

31. The method of claim 29, wherein the composition further comprises at least one non-fouling moiety.

32. The method of claim 29, wherein the composition further comprises at least one biobeneficial material.

33. The method of claim 29, wherein the composition further comprises at least one biologically active agent selected from antiproliferative, antineoplastic, antimitotic, anti-inflammatory, antiplatelet, anticoagulant, antifibrin, antithrombin, antibiotic, antiallergic and antioxidant substances.

34. The method of claim 33, wherein the at least one biologically active agent is selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof.

35. The method of claim 29, wherein the material is a coating disposed over at least a portion of the implantable device.

36. The method of claim 29, wherein the implantable device is selected from stents, grafts, stent-grafts, catheters, leads and electrodes, clips, shunts, closure devices, valves, and particles.

37. The method of claim 36, wherein the implantable device is a stent.

38. A composition comprising a biodegradable copolymer, wherein the biodegradable copolymer:
   is polymerized from dioxanone and three additional different ester-, carbonate- or ether based monomers;
   has a crystallinity of about 80% or less;
   has a glass transition temperature, $T_g$ from about −100° C. to about 100° C.;
   has a polymer number-average molecular weight M from about 10 kDa to about 1,500 kDa; and
   completely or substantially completely degrades within about 24 months when exposed to physiological conditions;
   wherein the additional ester-, carbonate- or ether-based monomers are selected from glycolide (GA), α-bromo-γ-butyrolactone, α-bromo-γ-valerolactone, homoserine lactone $C_2$-$C_{14}$ amide, mevalonolactone, 1,3-dioxolan-2-one, 4-methyl-1,3-dioxolan-2-one, 4-methoxymethyl-1,3-dioxolan-2-one, 4-chloro-1,3-dioxolan-2-one, 4-phenyl-1,3-dioxolan-2-one, 4-vinyl-1,3-dioxolan-2-one, trimethylene carbonate (TMC), β-propiolactone (PL), β-butyrolactone (BL), δ-valerolactone (VL), ε-caprolactone (CL), and propylene oxide (PPO).

39. The composition of claim 38, wherein the copolymer:
   has a crystallinity from about 5% to about 70%;
   has a $T_g$ from about −60° C. to about 60° C.;
   has an $M_n$ from about 20 kDa to about 1,000 kDa; and
   completely or substantially completely degrades within about 12 months when exposed to physiological conditions.

40. The composition of claim 39, wherein the copolymer:
   has a crystallinity from about 10% to about 60%;
   has a $T_g$ from about −30° C. to about 30° C.;
   has an $M_n$ from about 30 kDa to about 700 kDa; and
   completely or substantially completely degrades within about 6 months when exposed to physiological conditions.

41. The composition of claim 38, wherein dioxanone and the additional ester-, carbonate- or ether-based monomers each independently have from about 5 to about 5,000 monomer units.

42. The composition of claim 38, wherein the copolymer is P(DS-GA-CL-TMC).

43. The composition of claim 38, further comprising at least one additional biocompatible moiety selected from poly (ethylene oxide), polypropylene glycol), poly(tetramethylene glycol), poly(ethylene oxide-co-propylene oxide), ε-caprolactone, β-butyrolactone, δ-valerolactone, glycolide, poly (N-vinyl pyrrolidone), poly(acrylamide methyl propane sulfonic acid) and salts thereof, poly(styrene sulfonate), sulfonated dextran, polyphosphazenes, poly(orthoesters), poly (tyrosine carbonate), sialic acid, hyaluronic acid, copolymers of poly(ethylene glycol) (PEG) with hyaluronic acid, heparin, copolymers of PEG with heparin, graft copolymers of poly (L-lysine) and PEG, and copolymers thereof.

44. The composition of claim 38, further comprising at least one non-fouling moiety selected from polyethylene glycol, polypropylene glycol, polypropylene oxide-co-PEG, poly(2-hydroxyethyl methacrylate), poly(vinyl alcohol), polyalkene oxides, poly(n-propylmethacrylamide), poly(N-vinyl-2-pyrrolidone), sulfonated polystyrene, dextran, sulfonated dextran, dextrin, hyaluronic acid, and sodium hyaluronate.

45. The composition of claim 38, further comprising at least one biobeneficial material selected from fibrin, fibrinogen, cellulose, starch, pectin, chitosan, elastin, gelatin, alginate and conjugates thereof, collagen and conjugates thereof, hyaluronan, hyaluronic acid, and sodium hyaluronate.

46. The composition of claim 38, further comprising at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, and a combination thereof.

47. A coating of an implantable device comprising the composition of claim 38.

48. The coating of claim 47, which has a thickness of ≤ about 10 micron and completely or substantially completely degrades within about 12 months when exposed to physiological conditions.

49. An implantable device formed of a material comprising the composition of claim 38.

50. The device of claim 49, which is selected from stents, grafts, stent-grafts, catheters, leads and electrodes, clips, shunts, closure devices, valves, and particles.

51. The device of claim 50, which is a stent.

52. A method of preparing the composition of claim 38, comprising performing ring-opening polymerization (ROP) reactions with an initiator, dioxanone and three additional different ester-, carbonate-, or ether-based monomers, wherein the initiator has one or two active hydroxyl, amino, or thio end groups.

53. A method of fabricating an implantable device, comprising forming the device of a material comprising the composition of claim 38.

54. The method of claim 53, comprising depositing the material as a coating over at least a portion of the implantable device.

55. A method of treating a condition or disorder in a patient, comprising implanting in the patient an implantable device formed of a material comprising the composition of claim 38, wherein the condition or disorder is selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction.

56. The method of claim 55, wherein the composition further comprises at least one additional biocompatible moiety, one non-fouling moiety, or one biobeneficial material.

57. The method of claim 55, wherein the composition further comprises at least one biologically active agent selected from antiproliferative, antineoplastic, antimitotic, anti-inflammatory, antiplatelet, anticoagulant, antifibrin, antithrombin, antibiotic, antiallergic and antioxidant substances.

58. The method of claim 57, wherein the at least one biologically active agent is selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof.

59. The method of claim 55, wherein the material is a coating disposed over at least a portion of the implantable device.

60. The method of claim 55, wherein the implantable device is selected from stents, grafts, stent-grafts, catheters, leads and electrodes, clips, shunts, closure devices, valves, and particles.

61. The method of claim 60, wherein the implantable device is a stent.

* * * * *

```
SEQUENCE LISTING

<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 1

Arg Ala Arg Ala Asp Ala Asp Ala Arg Ala Arg Ala Asp Ala Asp Ala
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (20)..(20)
<223> OTHER INFORMATION: AMIDATION

<400> SEQUENCE: 2

Val Lys Val Lys Val Lys Val Lys Val Pro Pro Thr Lys Val Lys Val
1               5                   10                  15

Lys Val Lys Val
            20

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 3

Ala Glu Ala Glu Ala Lys Ala Lys Ala Glu Ala Glu Ala Lys Ala Lys
1               5                   10                  15
```

```
<210> SEQ ID NO 4
<211> LENGTH: 13
<212> TYPE: PRT
<213> ORGANISM: Artificial Sequence
<220> FEATURE:
<223> OTHER INFORMATION: Synthetic peptide

<400> SEQUENCE: 4

Asp Val Asp Val Pro Asp Gly Asp Ser Leu Ala Trp Gly
1               5                   10
```